United States Patent
Kovacs et al.

(10) Patent No.: US 11,819,417 B2
(45) Date of Patent: Nov. 21, 2023

(54) PATIENT-SPECIFIC AUGMENTED GLENOID SYSTEMS AND METHODS

(71) Applicant: Biomet Manufacturing, LLC, Warsaw, IN (US)

(72) Inventors: Michael Francis Kovacs, Warsaw, IN (US); Thomas M. Vanasse, Gainesville, FL (US); Lawrence Gulotta, Chappaqua, NY (US)

(73) Assignee: Biomet Manufacturing, LLC, Warsaw, IN (US)

( * ) Notice: Subject to any disclaimer, the term of this patent is extended or adjusted under 35 U.S.C. 154(b) by 463 days.

(21) Appl. No.: 17/025,200

(22) Filed: Sep. 18, 2020

(65) Prior Publication Data

US 2021/0000605 A1    Jan. 7, 2021

Related U.S. Application Data

(62) Division of application No. 16/022,248, filed on Jun. 28, 2018, now Pat. No. 10,806,591, which is a
(Continued)

(51) Int. Cl.
*A61B 17/17*        (2006.01)
*A61F 2/40*        (2006.01)
(Continued)

(52) U.S. Cl.
CPC ............ *A61F 2/40* (2013.01); *A61B 17/1684* (2013.01); *A61B 17/1739* (2013.01);
(Continued)

(58) Field of Classification Search
CPC ............ A61B 17/1739; A61B 17/1684; A61B 17/1778
See application file for complete search history.

(56) References Cited

U.S. PATENT DOCUMENTS 5,030,219 A  *  7/1991  Matsen, III ........ A61B 17/1778
                                                                606/86 R
5,769,856 A  *  6/1998  Dong ................. A61B 17/1778
                                                                606/80
(Continued)

FOREIGN PATENT DOCUMENTS

CN        102137638 A      7/2011
CN        103442666 A     12/2013
(Continued)

OTHER PUBLICATIONS

"Chinese Application Serial No. 201680034735.3, Office Action dated Oct. 16, 2020", (W/ English Translation), 15 pgs.
(Continued)

*Primary Examiner* — David W Bates
(74) *Attorney, Agent, or Firm* — SCHWEGMAN LUNDBERG & WOESSNER, P.A.

(57) ABSTRACT

A glenoid implant comprises a body comprising: an articular surface and a scapula-engaging surface, the scapula-engaging surface including first and second portions angled relative to each other; and a fixation feature extending from the scapula-engaging surface. A method comprises: forming a planar bone surface at a glenoid using a guide pin; forming a first bore into the glenoid located near the guide pin; forming a second bore into the glenoid offset from the first bore; inserting an augment ream guide into the first and second bores; and forming an angled bone surface at the glenoid relative to the planar bone surface using the augment ream guide. A ream guide comprises: a base having first and second surfaces; a bone peg extending from the first surface; an alignment peg spaced from the bone peg; and a guide peg extending from the second surface at an oblique angle to the bone peg.

17 Claims, 14 Drawing Sheets

Related U.S. Application Data division of application No. 15/136,552, filed on Apr. 22, 2016, now Pat. No. 10,034,757.

(60) Provisional application No. 62/152,304, filed on Apr. 24, 2015.

(51) Int. Cl.
*A61B 17/16* (2006.01)
*A61F 2/46* (2006.01)
*A61F 2/30* (2006.01)
*A61B 90/00* (2016.01)

(52) U.S. Cl.
CPC ........ *A61B 17/1778* (2016.11); *A61F 2/4081* (2013.01); *A61F 2/4612* (2013.01); *A61B 2090/036* (2016.02); *A61F 2002/3023* (2013.01); *A61F 2002/30617* (2013.01); *A61F 2002/30736* (2013.01); *A61F 2002/30774* (2013.01); *A61F 2002/30878* (2013.01)

(56) References Cited

U.S. PATENT DOCUMENTS

| | | |
|---|---|---|
| 5,800,551 A * | 9/1998 | Williamson ........ A61F 2/30724 623/19.11 |
| 6,120,507 A | 9/2000 | Allard et al. |
| 6,406,495 B1 | 6/2002 | Schoch |
| 6,699,289 B2 | 3/2004 | Iannotti et al. |
| 7,753,959 B2 | 7/2010 | Berelsman et al. |
| 7,892,287 B2 | 2/2011 | Deffenbaugh |
| 7,927,335 B2 | 4/2011 | Deffenbaugh et al. |
| 8,048,161 B2 | 11/2011 | Guederian et al. |
| 8,241,366 B2 | 8/2012 | Roche et al. |
| 8,556,901 B2 | 10/2013 | Anthony et al. |
| 8,870,962 B2 | 10/2014 | Roche et al. |
| 9,233,003 B2 | 1/2016 | Roche et al. |
| 9,498,345 B2 | 11/2016 | Burkhead, Jr. et al. |
| 9,629,725 B2 | 4/2017 | Gargac et al. |
| 9,844,440 B2 | 12/2017 | Kovacs et al. |
| 9,955,984 B2 * | 5/2018 | Winslow ............ A61B 17/1778 |
| 10,034,757 B2 | 7/2018 | Kovacs et al. |
| 10,806,591 B2 | 10/2020 | Kovacs et al. |
| 2006/0015188 A1 * | 1/2006 | Grimes ................. A61F 2/3601 623/23.22 |
| 2006/0074430 A1 * | 4/2006 | Deffenbaugh ..... A61B 17/1778 606/87 |
| 2007/0225714 A1 * | 9/2007 | Gradl ................... A61B 17/746 606/326 |
| 2009/0125113 A1 | 5/2009 | Guederian et al. |
| 2009/0270867 A1 | 10/2009 | Poncet |
| 2010/0161066 A1 | 6/2010 | Iannotti et al. |
| 2010/0234959 A1 | 9/2010 | Roche et al. |
| 2010/0241235 A1 | 9/2010 | Basamania et al. |
| 2010/0268238 A1 * | 10/2010 | Sikora ................... A61F 2/4081 606/87 |
| 2011/0029088 A1 * | 2/2011 | Rauscher ........... A61B 17/1778 623/19.11 |
| 2011/0035013 A1 | 2/2011 | Winslow et al. |
| 2011/0144651 A1 | 6/2011 | Deffenbaugh et al. |
| 2011/0144758 A1 | 6/2011 | Deffenbaugh |
| 2011/0213371 A1 | 9/2011 | Anthony et al. |
| 2011/0213372 A1 * | 9/2011 | Keefer ................ A61B 17/1735 606/85 |
| 2012/0078258 A1 * | 3/2012 | Lo ...................... A61B 17/1778 606/87 |
| 2012/0109137 A1 * | 5/2012 | Iannotti ............. A61B 17/1728 606/87 |
| 2012/0130499 A1 | 5/2012 | Long |
| 2012/0221111 A1 | 8/2012 | Burkhead, Jr. et al. |
| 2012/0239051 A1 * | 9/2012 | De Wilde ............. A61F 2/4081 606/96 |
| 2012/0276509 A1 | 11/2012 | Iannotti et al. |
| 2013/0110116 A1 | 5/2013 | Kehres et al. |
| 2013/0150975 A1 | 6/2013 | Iannotti et al. |
| 2013/0236874 A1 * | 9/2013 | Iannotti .................. B29C 39/02 434/274 |
| 2013/0309031 A1 * | 11/2013 | Winslow ............ A61B 17/1633 408/1 R |
| 2014/0005789 A1 | 1/2014 | Chavarria et al. |
| 2014/0031945 A1 | 1/2014 | Baptista et al. |
| 2014/0066933 A1 * | 3/2014 | Ek .......................... A61F 2/4081 606/80 |
| 2014/0194879 A1 | 7/2014 | Koka |
| 2014/0257304 A1 * | 9/2014 | Eash .................. A61B 17/1778 606/87 |
| 2014/0257499 A1 | 9/2014 | Winslow et al. |
| 2014/0277517 A1 | 9/2014 | Winslow |
| 2015/0150688 A1 | 6/2015 | Vanasse et al. |
| 2015/0305877 A1 | 10/2015 | Gargac et al. |
| 2015/0374502 A1 * | 12/2015 | Hodorek ................ A61B 17/17 606/80 |
| 2016/0045207 A1 * | 2/2016 | Kovacs .............. A61B 17/1631 606/80 |
| 2016/0045323 A1 | 2/2016 | Kovacs et al. |
| 2016/0199074 A1 * | 7/2016 | Winslow ............ A61B 17/1778 606/80 |
| 2016/0256222 A1 | 9/2016 | Walch |
| 2016/0310285 A1 | 10/2016 | Kovacs et al. |
| 2018/0303618 A1 | 10/2018 | Kovacs et al. |
| 2019/0015193 A1 * | 1/2019 | Kovacs .................... A61F 2/08 |
| 2020/0000601 A1 | 1/2020 | Hodorek et al. |

FOREIGN PATENT DOCUMENTS

| | | |
|---|---|---|
| CN | 203328873 U | 12/2013 |
| CN | 108135707 A | 6/2018 |
| CN | 113143394 A | 7/2021 |
| EP | 1639949 A1 | 3/2006 |
| EP | 1776935 A1 | 4/2007 |
| EP | 2335655 A1 | 6/2011 |
| EP | 2586387 A1 | 5/2013 |
| EP | 3179927 A2 | 6/2017 |
| JP | H07508203 A | 9/1995 |
| JP | 2001526083 A | 12/2001 |
| JP | 2006500096 A | 1/2006 |
| JP | 2018516634 A | 6/2018 |
| JP | 2020054840 A | 4/2020 |
| WO | WO-2015056097 A1 | 4/2015 |
| WO | WO-2016172572 A1 | 10/2016 |

OTHER PUBLICATIONS

"Chinese Application Serial No. 201680034735.3, Response filed Dec. 28, 2020 to Office Action dated Oct. 16, 2020", w/ English claims, 12 pgs.

"European Application Serial No. 19211567.3, Extended European Search Report dated May 6, 2021", 10 pgs.

"European Application Serial No. 19211567.3, Partial European Search Report dated Feb. 4, 2021", 11 pgs.

"European Application Serial No. 19211567.3, Response filed Dec. 2, 2021 to Extended (European Search Report dated May 6, 2021", 15 pgs.

"Japanese Application Serial No. 2017-555529, Notification of Reasons for Refusal dated Dec. 10, 1020", w/ English Translation, 6 pgs.

"Japanese Application Serial No. 2017-555529, Response filed Feb. 10, 2021 to Notification of Reasons for Refusal dated Dec. 10, 2020", w/ English claims, 9 pgs.

"Japanese Application Serial No. 2019-230613, Notification of Reasons for Refusal dated Dec. 15, 2020", (W/ English Translation), 6 pgs.

"Japanese Application Serial No. 2019-230613, Response filed Mar. 12, 2021 to Notification of Reasons for Refusal dated Dec. 15, 2020", w/ English claims, 7 pgs.

"U.S. Appl. No. 15/136,552, Corrected Notice of Allowance dated Feb. 13, 2018", 5 pgs.

"U.S. Appl. No. 15/136,552, Corrected Notice of Allowance dated Apr. 2, 2018", 4 pgs.

(56) References Cited

OTHER PUBLICATIONS

"U.S. Appl. No. 15/136,552, Non Final Office Action dated Aug. 7, 2017", 10 pgs.
"U.S. Appl. No. 15/136,552, Notice of Allowance dated Jan. 17, 2018", 8 pgs.
"U.S. Appl. No. 15/136,552, Response filed Jul. 12, 2017 to Restriction Requirement dated May 23, 2017", 7 pgs.
"U.S. Appl. No. 15/136,552, Response filed Nov. 3, 2017 to Non Final Office Action dated Aug. 7, 2017", 15 pgs.
"U.S. Appl. No. 15/136,552, Restriction Requirement dated May 23, 2017", 7 pgs.
"U.S. Appl. No. 16/022,248, Corrected Notice of Allowability dated Aug. 10, 2020", 4 pgs.
"U.S. Appl. No. 16/022,248, Notice of Allowance dated Jun. 17, 2020", 9 pgs.
"U.S. Appl. No. 16/022,248, Preliminary Amendment filed Jul. 30, 2018", 7 pgs.
"Australian Application Serial No. 2016250842, First Examination Report dated Nov. 29, 2019", 4 pgs.
"Australian Application Serial No. 2016250842, Response filed Mar. 31, 2020 to First Examination Report dated Nov. 29, 2019", 17 pgs.
"Canadian Application Serial No. 2,983,650, Office Action dated Mar. 11, 2019", 4 pgs.
"Canadian Application Serial No. 2,983,650, Office Action dated Jul. 9, 2018", 3 pgs.
"Canadian Application Serial No. 2,983,650, Response filed Jan. 9, 2019 to Office Action dated Jul. 9, 2018", 8 pgs.
"Canadian Application Serial No. 2,983,650, Response filed Sep. 10, 2019 to Office Action dated Mar. 11, 2019", 5 pgs.
"Chinese Application Serial No. 201680034735.3, Office Action dated Feb. 27, 2019", w/ English Translation, 5 pgs.
"Chinese Application Serial No. 201680034735.3, Office Action dated May 25, 2020", (W/ English Translation), 11 pgs.
"Chinese Application Serial No. 201680034735.3, Office Action dated Nov. 1, 2019", w/ English Translation, 13 pgs.
"Chinese Application Serial No. 201680034735.3, Response filed Jan. 16, 2020 to Office Action dated Nov. 1, 2019", w/ English claims, 8 pgs.
"Chinese Application Serial No. 201680034735.3, Response filed Jul. 10, 2019 to Office Action dated Feb. 27, 2019", w/ English claims, 6 pgs.
"Chinese Application Serial No. 201680034735.3, Response filed Jul. 15, 2020 to Office Action dated May 25, 2020", (W/ English Translation of Claims), 7 pgs.
"European Application Serial No. 16722982.2, Response filed Aug. 13, 2018 to Office Action dated Feb. 1, 2018", 15 pgs.
"International Application Serial No. PCT/US2016/028972, International Preliminary Report on Patentability dated Nov. 2, 2017", 10 pgs.
"International Application Serial No. PCT/US2016/028972, International Search Report dated Sep. 26, 2016", 6 pgs.
"International Application Serial No. PCT/US2016/028972, Invitation to Pay Add'l Fees and Partial Search Report dated Jul. 25, 2016", 7 pgs.
"International Application Serial No. PCT/US2016/028972, Written Opinion dated Sep. 26, 2016", 8 pgs.
"Japanese Application Serial No. 2017-555529, Examiners Decision of Final Refusal dated Aug. 20, 2019", w/ English Translation, 5 pgs.
"Japanese Application Serial No. 2017-555529, Office Action dated Nov. 13, 2018", w/ English translation, 5 pgs.
"Japanese Application Serial No. 2017-555529, Response filed Apr. 24, 2019 to Office Action dated Nov. 13, 2018", w/ English claims, 10 pgs.
Neer, Charles S., et al., "Glenoid Bone-Grafting in Total Shoulder Arthroplasty", The Journal of Bone and Joint Surgery, vol. 70-A, No. 8,, (Sep. 1998), pp. 1154-1162.
U.S. Appl. No. 15/136,552 U.S. Pat. No. 10,034,757, filed Apr. 22, 2016, Patient-Specific Augmented Glenoid Systems and Methods.
U.S. Appl. No. 16/022,248, filed Jun. 28, 2018, Patient-Specific Augmented Glenoid Systems and Methods.
"European Application Serial No. 19211567.3, Communication Pursuant to Article 94(3) EPC dated Feb. 21, 2023", 4 pgs.
"European Application Serial No. 19211567.3, Response filed Jun. 29, 2023 to Communication Pursuant to Article 94(3) EPC dated Feb. 21, 2023", 14 pgs.

\* cited by examiner

PATIENT-SPECIFIC AUGMENTED GLENOID SYSTEMS AND METHODS

CLAIM OF PRIORITY

This patent application is a divisional of U.S. patent application Ser. No. 16/022,248, filed on Jun. 28, 2018, which is a divisional of U.S. patent application Ser. No. 15/136,552, filed on Apr. 22, 2016, now issued as U.S. Pat. No. 10,034,757, which claims the benefit of priority of Kovacs et al., U.S. Provisional Patent Application Ser. No. 62/152,304, entitled PATIENT SPECIFIC AUGMENTED GLENOID PREP," filed on Apr. 24, 2015, each of which are hereby incorporated by reference herein in its entirety.

TECHNICAL FIELD

This document pertains generally, but not by way of limitation, to systems and methods for preparing a bone for an orthopedic implant. More particularly, this disclosure relates to, but not by way of limitation, preparing a bone surface to receive an orthopedic implant having an asymmetric bone-engaging surface.

BACKGROUND

In cases of severe glenoid wear, it can be difficult to return the joint to near neutral version using a standard implant. In these instances, the surgeon has to compromise by putting in the component at a non-ideal version angel, removing significant amount of native bone to gain complete backside coverage of the glenoid base, or bone grafting to support the backside of the glenoid implant.

Recently, glenoid implants with augments have been developed as options for these cases with severe glenoid wear. For anatomic shoulder arthroplasty, augmented glenoid implants can include various stepped or contoured bone-contacting surfaces. However, many of these designs still require removal of a significant amount of bone.

Examples of glenoid implants are described in U.S. Pub. No. 2015/0150688 to Vanasse et al., U.S. Pat. No. 6,699,289 to Iannotti et al., U.S. Pat. No. 9,233,003 to Roche et al., and U.S. Pat. No. 7,753,959 to Berelsman et al.

OVERVIEW

The present inventors have recognized, among other things, that a problem to be solved can include the need to reduce the amount of bone removed when implanting glenoid implants. Furthermore, the present inventors have recognized that another problem to be solved can include the need to simplify bone preparation techniques when installing glenoid implants.

The present subject matter can help provide a solution to this problem, such as by providing augmented implants with angled, sloped and partially sloped bone-contacting surfaces, and instruments and methods for implanting such augmented implants, in patient-specific and non-patient specific embodiments.

A glenoid implant can comprise a body comprising: an articular surface configured to mate with or receive another component configured to mate with a complimentary component; and a scapula-engaging surface opposite the articular surface, the scapula engaging surface including first and second portions angled relative to each other; and a fixation feature extending from the scapula-engaging surface.

A method for implanting a scapular baseplate in a shoulder arthroplasty can comprise: inserting a guide pin into a glenoid of the scapula using a guide instrument; preparing a first portion of the glenoid to form a planar bone surface using the guide pin; forming a first bore into the glenoid located approximately at the guide pin; forming a second bore into the glenoid offset from the first bore; inserting an augment ream guide into the first bore and the second bore; and preparing a second portion of the glenoid to form an angled bone surface relative to the planar bone surface using the augment ream guide.

A ream guide for a shoulder arthroplasty procedure can comprise: a base having a first surface and a second surface; a bone peg extending perpendicularly from the first surface; an alignment peg extending from the first surface spaced from the bone peg; and a guide peg extending from the second surface opposite the bone peg at an oblique angle to the bone peg.

This overview is intended to provide an overview of subject matter of the present patent application. It is not intended to provide an exclusive or exhaustive explanation of the invention. The detailed description is included to provide further information about the present patent application.

Figure 1:
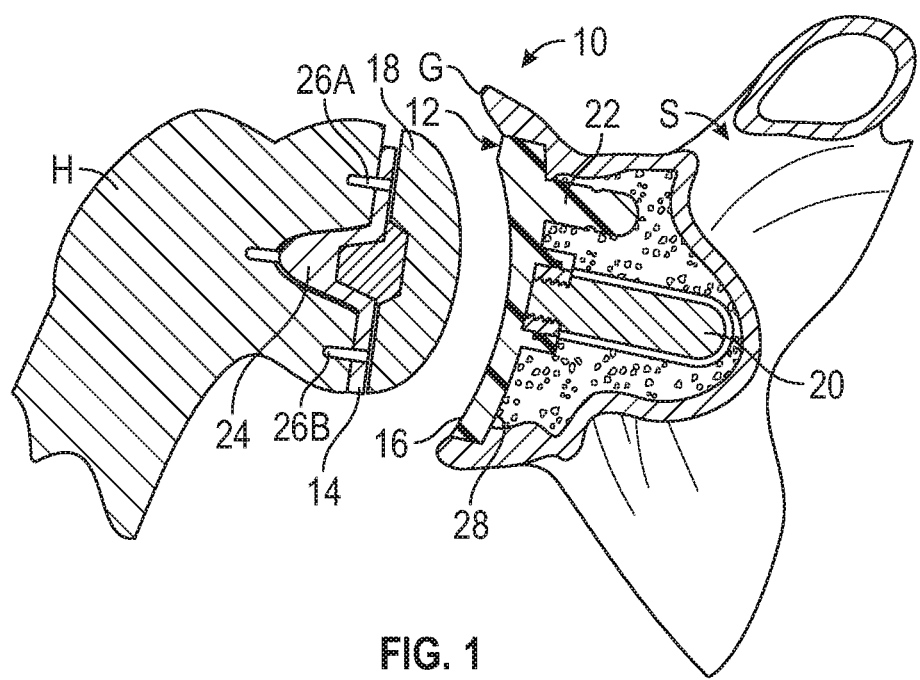
FIG. 1 is a cross-sectional view of a prior art anatomic shoulder replacement system comprising a glenoid implant for implanting in a scapula and a humeral head for implanting in a humerus.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 is a cross-sectional view of prior art anatomic shoulder implant 10 comprising implanted glenoid implant 12 and implanted humeral implant 14. Glenoid implant 12 can include glenoid 16 and humeral implant 14 can include humeral head 18. Glenoid implant 12 can be secured to glenoid G of scapula S using center post 20 and peripheral post 22. Humeral implant 14 can be secured to humerus H using any suitable means, such as center post 24 and fasteners 26A and 26B. Glenoid G of scapula S can typically be reamed to provide a single surface to engage bone surface 28 of glenoid implant 12. As can be seen, glenoid implant 12 can be typically of substantially uniform thickness and bone surface 28 typically can comprise a single smooth surface, other than the portions associated with center post 20 and peripheral post 22. These geometric features of glenoid implant 12 can sometimes unavoidably result in some amount of healthy bone being removed.

Figure 2:
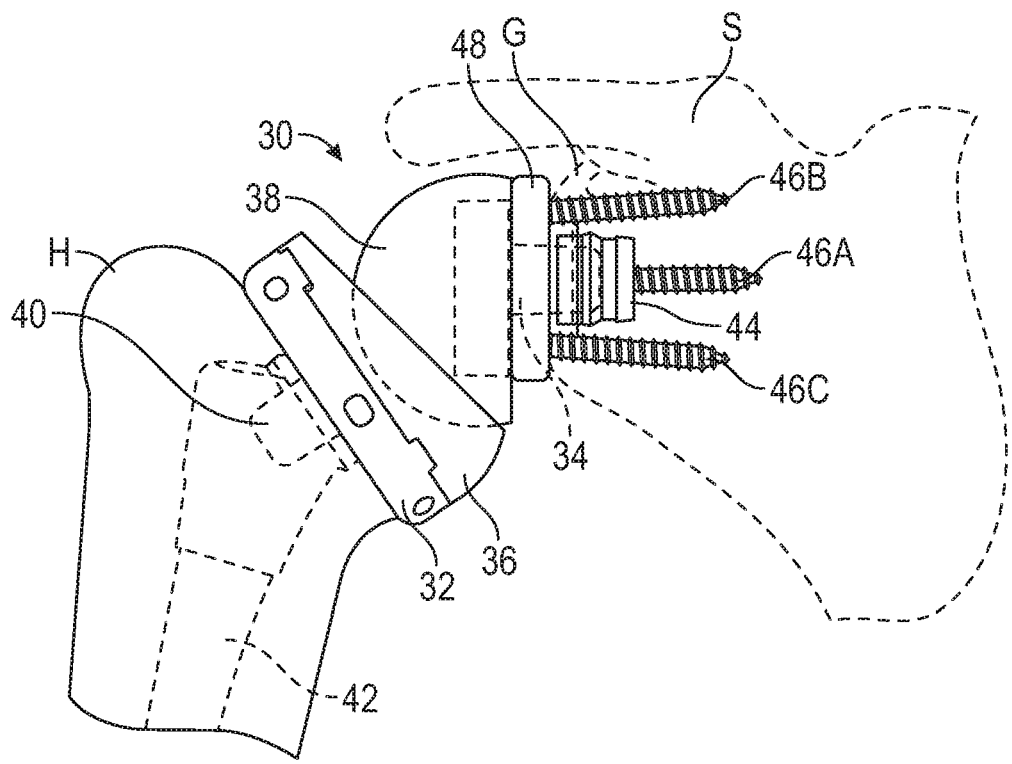
FIG. 2 is a cross-sectional view of a prior art reverse shoulder replacement system comprising a glenosphere baseplate for implanting in a scapula and a humeral tray and humeral implant for implanting in a humerus.

FIG. 2 is a cross-sectional view of prior art reverse shoulder implant 30 comprising implanted humeral tray 32 and implanted glenosphere baseplate 34. Humeral tray 32 can include polyethylene (PE) liner 36 and glenosphere baseplate 34 can include glenosphere 38. Humeral tray 32 can be secured to humerus H using any suitable means, such as center post 40 and stem 42. Glenosphere baseplate 34 can be secured to glenoid G of scapula S using center post 44 and fasteners 46A-46C. Baseplate 34 can be secured by other means, such as through the use of four peripheral screws and a center post. Glenoid G of scapula S can typically be reamed to provide a single surface to engage bone surface 48 of glenosphere baseplate 34. As can be seen, glenosphere baseplate 34 can be typically of substantially uniform thickness and bone surface 48 typically can comprise a single smooth surface, other than the portions associated with center post 44 and fasteners 46A-46C. These geometric features of glenosphere baseplate 34 can sometimes unavoidably result in some amount of healthy bone being removed.

Figure 3B:
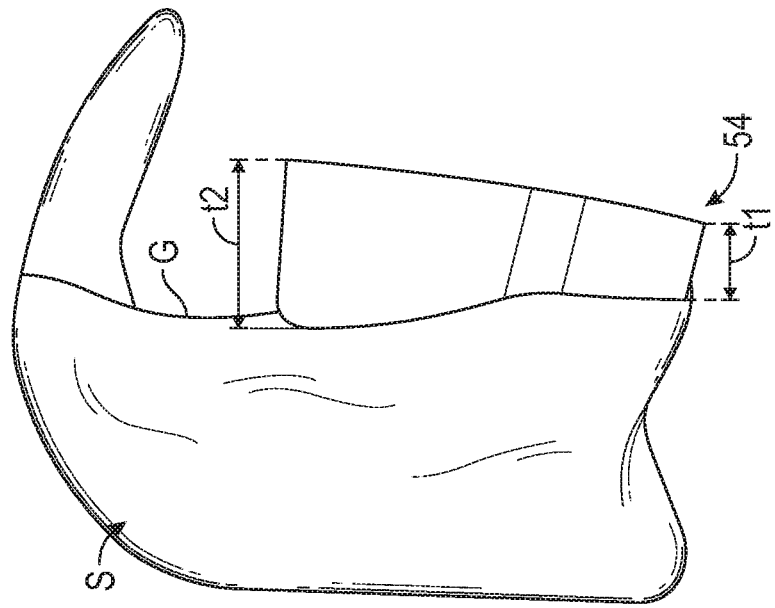
FIG. 3B is a perspective view of the augmented baseplate of FIG. 3A implanted on a scapula.
Figure 3A:
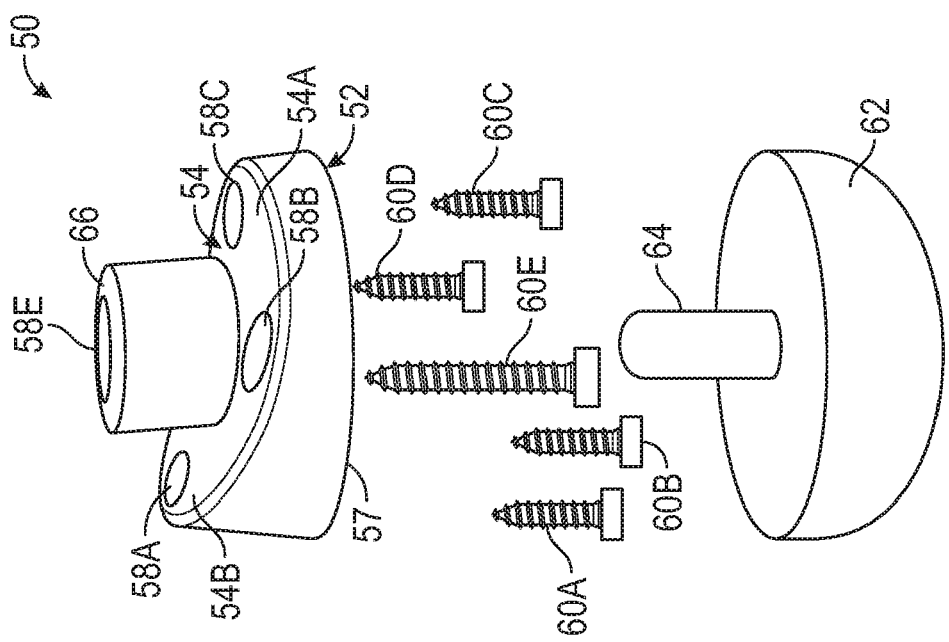
FIG. 3A is a perspective view of an augmented baseplate for a reverse shoulder implant having an angled bone surface with bores for receiving fixation fasteners and a glenosphere.

FIG. 3A is a perspective view of reverse shoulder implant 50 including augmented baseplate 52 having angled bone surface 54. Baseplate 52 can also include stem 56, mate face 57 and bores 58A-58E (56D shown in FIG. 10A) for receiving fixation fasteners 60A-60E. Angled bone surface 54 can include parallel surface 54A and oblique surface 54B. Implant 50 can also include glenosphere 62, which can include stem 64. Parallel surface 54A can be parallel to mate face 57, as well as distal surface 66 of stem 64. In various embodiments, baseplate 52 can be made of a porous material, such as a highly porous metal, Trabecular Metal®, or tantalum.

FIG. 3B is a perspective view of the augmented baseplate 52 of FIG. 3A implanted on scapula S. Glenoid G of scapula S can be prepared to mate with parallel surface 54A and oblique surface 54B, such as by reaming of glenoid G to form obliquely oriented planar bone surfaces. Oblique surface 54B can be located in any orientation of glenoid G. For example, oblique surface 54B can be located at superior, inferior, posterior or anterior portions on glenoid G, or at any intermediate orientation. The methods, instruments and tools described herein, particularly with reference to FIGS. 4A-10B, facilitate implantation of augmented baseplate 52 onto scapula S in such a manner so as to minimize bone removal and subsequently align augmented baseplate so that surfaces 54A and 54B mate flush with prepared surfaces of glenoid G.

Figure 4A:
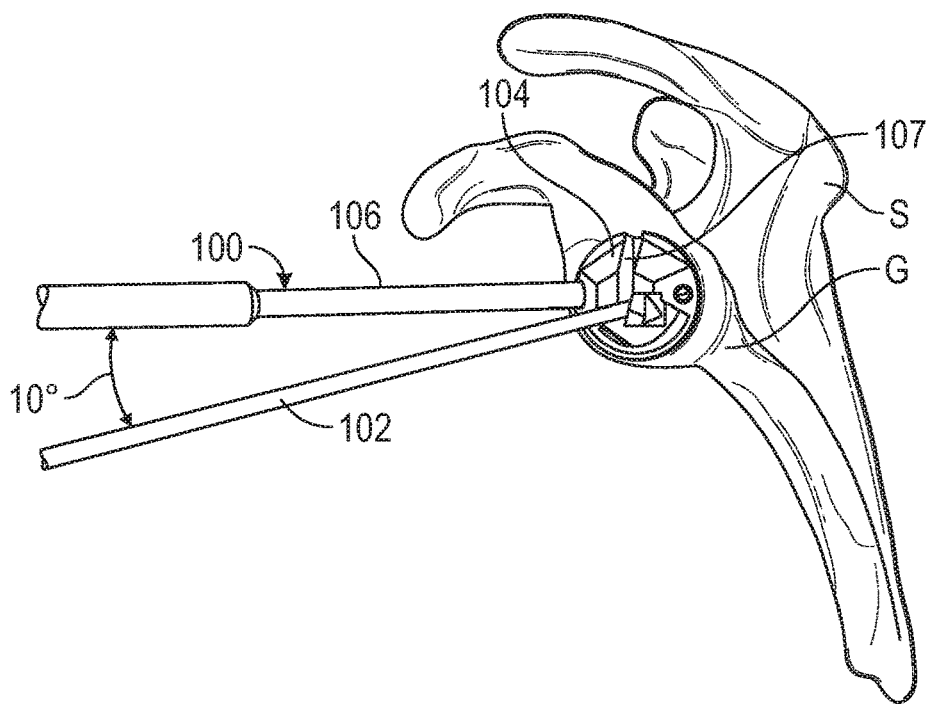
FIG. 4A is a perspective view of a standard glenoid guide instrument being used to insert a guide pin into a glenoid of a scapula.

FIG. 4A is a perspective view of standard (i.e. non-patient-specific) glenoid guide instrument 100 being used to insert guide pin 102 into glenoid G of scapula S. Instrument 100 can include pin placement guide 104 and glenoid guide handle 106.

The appropriate pin placement guide 104 can be selected based on the degree of glenoid erosion. For example, oblique surface 54B of augmented baseplate 52 (FIG. 3A) can be angled relative to parallel surface 54A at an angle of 10°, 20° or 30°. Thus, pin placement guide 104 can be made to substantially align guide pin 102 with to the central axis of the vault of glenoid G for 10°, 20°, or 30° baseplates. However a 10 degree inferior tilt can be built into placement guide 104. The appropriate pin placement guide 104 is selected to align guide pin 102, which can be a Steinman pin, in the desired version and inclination. Glenoid guide handle 106 can be attached to the appropriate augment pin placement guide 104 (10°, 20°, or 30°). In one example, a 3.2 mm Steinmann pin is used as guide pin 102 and is inserted into glenoid G at the desired angle and position, ensuring pin 102 engages or perforates the medial cortical wall. A completely secure guide pin is desired to ensure the subsequent used reamer has a stable cannula over which to ream.

When guide pin 102 is placed correctly within guide 104, guide pin 102 can lie flush with inferior groove 107. Pin placement guide 104 can be centered over the inferior portion of glenoid G. However, in glenoid deformity cases and situations with poor bone quality, guide pin 102 can be placed into the best possible bone stock.

Figure 4B:
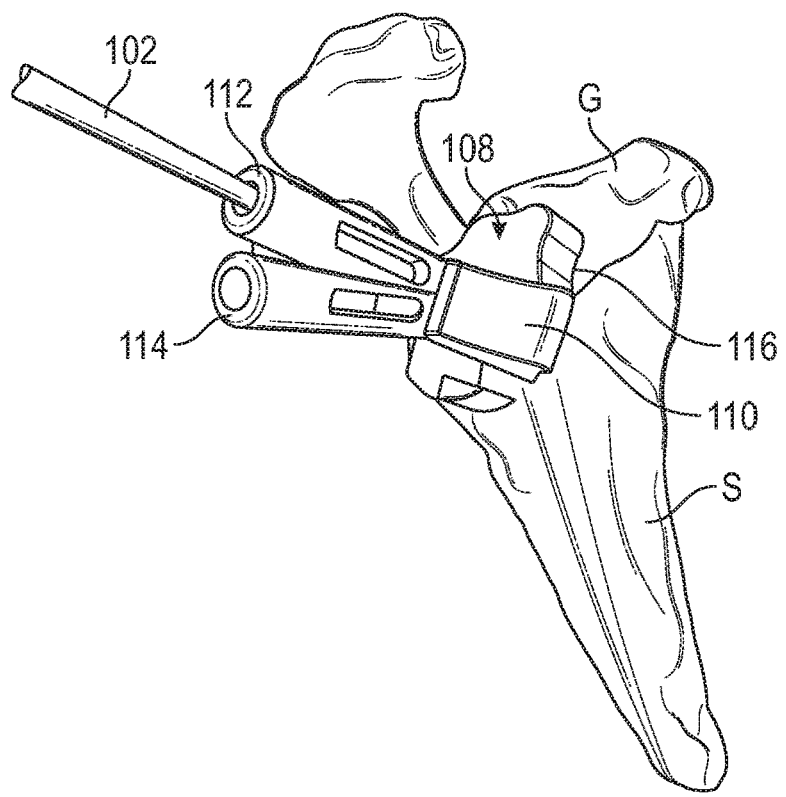
FIG. 4B is a perspective view of a patient-specific glenoid guide instrument being used to insert a guide pin into a glenoid of a scapula.

FIG. 4B is a perspective view of patient-specific glenoid guide instrument 108 being used to insert guide pin 102 into glenoid G of scapula S. Patient-specific glenoid guide instrument 108 can include base 110, anatomic guide sleeve 112 and reverse guide sleeve 114. Base 110 can include patient-specific bone surface 116. At least a portion of the scapula-engaging bone surface 116 is configured to mirror and conform to a surface of scapula S of a specific patient based on a three-dimensional (3D) model of scapula S. In one embodiment, patient-specific glenoid guide instrument 108 can comprise a Signature guide tool commercially available from Zimmer Biomet. One or more examples of a Signature guide tool are described in U.S. Pub. No. 2013/0110116 to Kehres et al., which is hereby incorporated by this reference in its entirety for all purposes.

Figure 5A:
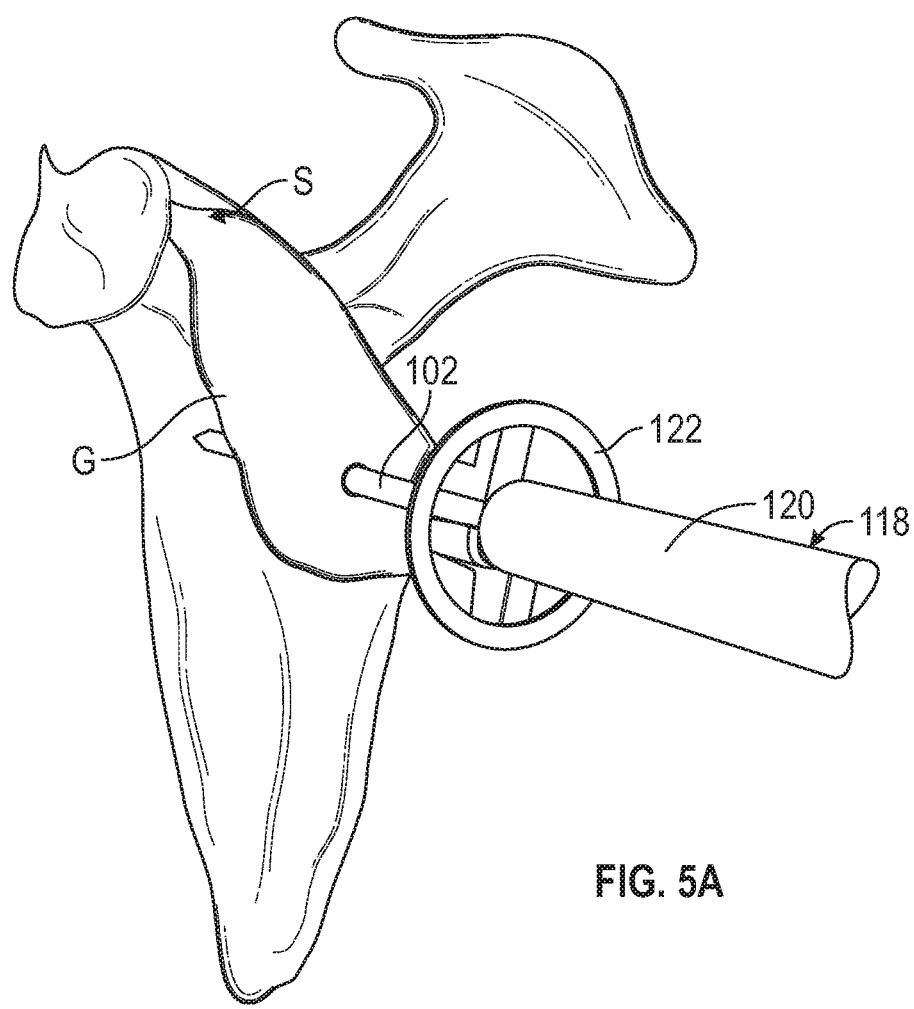
FIG. 5A is a perspective view of a face reamer being advanced along the guide pin of FIG. 4A or 4B to partially ream the scapula.

FIG. 5A is a perspective view of face reamer 118 being advanced along guide pin 102 of FIG. 4A or 4B to partially ream glenoid G of scapula S. Face reamer 118 includes cannulated shaft 120 and reamer head 122.

First, the non-deficient half or portion of the native surfaces of glenoid G can be prepared, before the deficient, or damaged half of portion of the surfaces of glenoid G are prepared. Cannulated shaft 120 of face reamer 118 can be positioned over guide pion 102 and rotated to remove bone from glenoid G. In one example, bone can be reamed on at least 50 percent of the face of glenoid G. Due to the 10 degree inferior tilt of guide pin 102, inferior ridge R may be evident with bone also prepared opposite of the glenoid erosion.

Figure 5B:
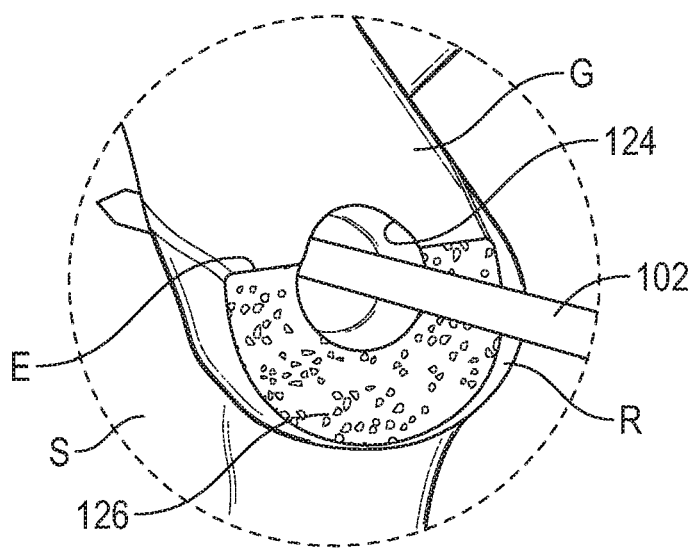
FIG. 5B is a close up view of the partially reamed scapula of FIG. 5A with a guide pin inserted therein.

FIG. 5B is a close up view of partially reamed scapula S of FIG. 5A with guide pin 102 inserted therein. After face reamer 118 is removed, guide pin 102 remains seated within glenoid G. Face reamer 118 can produce central bore 124 and first reamed surface 126. Central bore 124 can be centered around guide pin 102 and first reamed surface 126 can include edge E that extends across central bore 124 at the level of guide pin 102.

Figure 6A:
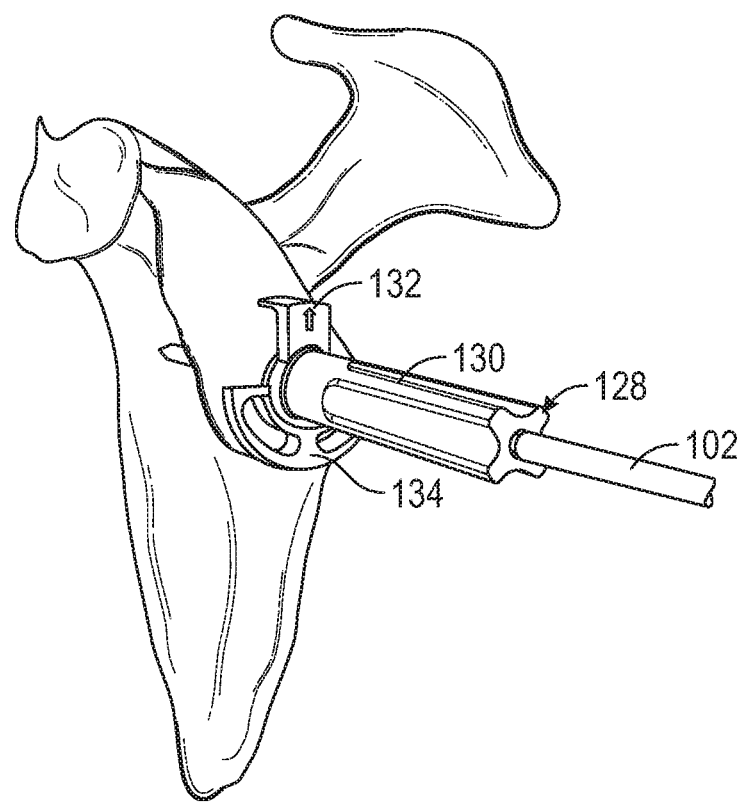
FIG. 6A is a perspective view of an augment sizer being advanced along the guide pin of FIG. 4A or 4B to measure the size of the partially reamed scapula.
Figure 6B:
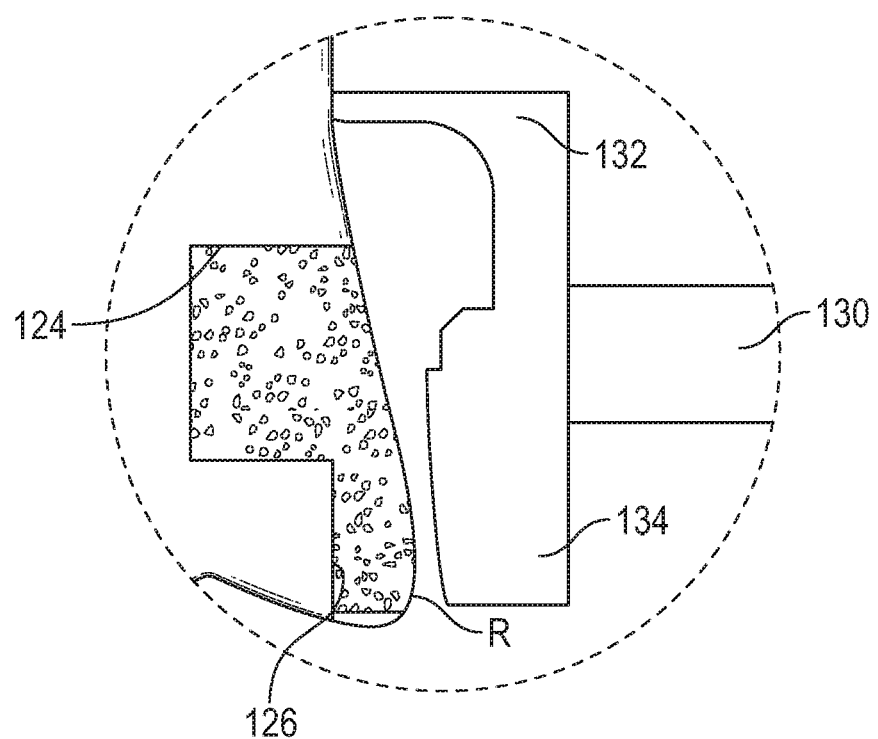
FIG. 6B is a side cross-sectional view of the augment sizer of FIG. 6A correctly seated with a properly reamed glenoid.

FIG. 6A is a perspective view of augment sizer 128 being advanced along guide pin 102 of FIG. 4A or 4B to measure the size of partially reamed scapula S. FIG. 6B is a side cross-sectional view of augment sizer 128 of FIG. 6A correctly seated with properly reamed glenoid G. Augment sizer 128 can include shaft 130, finger 132 and base 134, and can come in different sizes (10°, 20° and/or 30°) for the different sized baseplates 52.

It is desirable that glenoid G be reamed to at least fifty percent to ensure glenoid G is prepared to fully support parallel face 54A of augment baseplate 52. Reaming beyond fifty percent can remove additional bone which is not necessary for augment preparation. As discussed below, in one example, using augment sizer 128 before reaming, a line can be drawn at the fifty percent line on the face of glenoid G (which can coincide with edge E), such as with a blue marker or bovie, and reaming is performed until the line disappears to ensure glenoid G is reamed to the desired precision level.

Augment sizer 128 can be used to measure and ensure at least fifty percent of the face of glenoid G has been reamed. After fifty percent of the face of glenoid G is reamed, a central channel of shaft 130 can be slid onto guide pin 102 until finger 132 engages the partially reamed scapula S.

After the glenoid face has been reamed at least 50 percent, the different sized augment sizers 128 (10°, 20° and/or 30°) can be used to determine which size augment baseplate 52. First the 10° augment sizer can be placed on the fifty percent reamed glenoid G. First, it can be evaluate whether or not the 10° finger 132 touches the non-reamed (defect) portion of the face of glenoid G or sits proud. If the 10° augment sizer finger 132 sits proud, off the face of the defect, then glenoid G can be re-evaluated with the 20° augment sizer. If the 10° augment sizer finger 132 touches the defect yet sits proud, off the face of the fifty percent reamed surface, this is the size of augmented baseplate 52 that can or should be chosen. This algorithm can be continued until the optimal augment is found. There may be circumstances where the defect is in between sizes, and the surgeon can make a judgment call as to either go to a taller augment, reaming the defect side, or to go to a shorter augment, reaming the high side of glenoid G. Once fifty percent of the face of glenoid G is reamed, face reamer 118 can be removed from guide pin 102.

As mentioned, augment sizer 128 can also be used to determine which size (10°, 20° or 30°) augmented baseplate 52 should be used before scapula is reamed. Augment sizer 128 can come in three sizes (10°, 20° or 30°) to correspond the differently sized augmented baseplates 52. Augment sizer 128 can be positioned over guide pin 102 to engage the face of glenoid G. Augment sizer 128 can be dialed (e.g. rotated on guide pin 102) to position finger 132 in the appropriated direction to allow the maximum defect to be removed and augmented baseplate 52 will lie in the desired orientation. The correctly sized augment sizer will have both finger 132 and base 134 engage glenoid G. As mentioned, a bovie or surgical marker can be used to mark the fifty percent line on the face of glenoid G, as this will be used in the subsequent step to determine sufficient ream depth, just described.

Figure 7A:
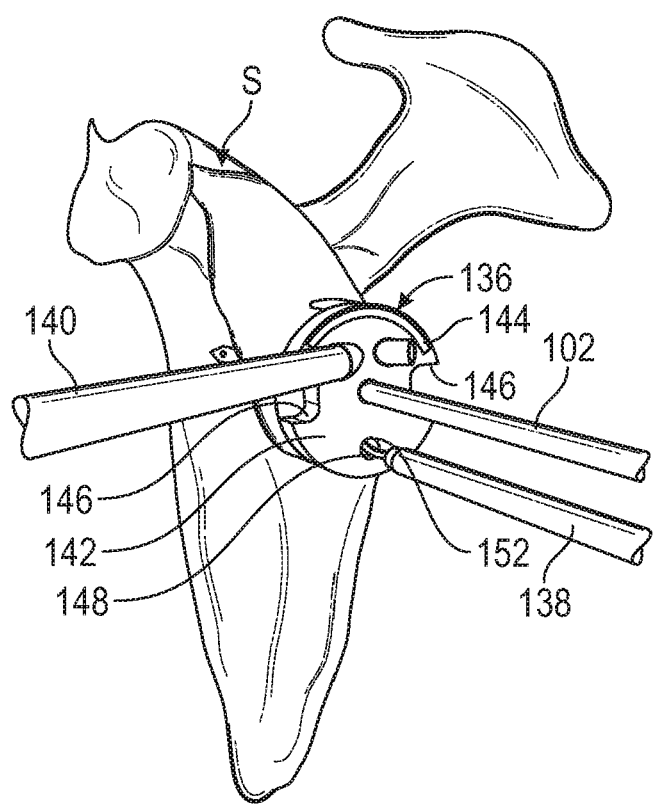
FIG. 7A is a perspective view of an alignment peg drill guide being advanced along the guide pin of FIG. 4A or 4B in order to drill an alignment hole in the partially reamed scapula.
Figure 7B:
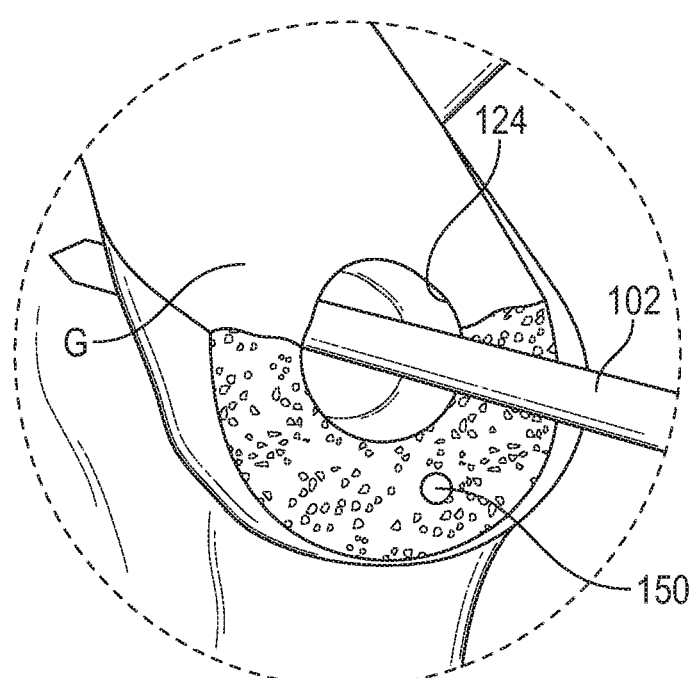
FIG. 7B is a close up view of the partially reamed scapula of FIG. 5A including an alignment hole produced using the drill guide of FIG. 7A.

FIG. 7A is a perspective view of alignment peg drill guide 136 being advanced along guide pin 102 of FIG. 4A or 4B in order to drill an alignment hole in the partially reamed scapula using drill bit 138. Alignment peg drill guide 136 can comprise handle shaft 140, baseplate 142, half-circle etch 144, windows 146 and guide hole 148. FIG. 7B is a close up view of the partially reamed scapula S of FIG. 5A including alignment hole 150 produced using drill guide 136 of FIG. 7A.

Base plate 142 can be positioned on glenoid G with the half-circle etch 144 in the exact location where the augment is desired. In one example, at least a portion of the scapula-engaging surface of base plate 142 can be configured to mirror and conform to a surface of scapula S of a specific patient based on a three-dimensional (3D) model of scapula S. Windows 146 can be referenced and centered on edge E of the fifty percent reamed glenoid. Once properly oriented, drill bit 138 can be inserted into guide hole 148 in baseplate 142 and glenoid G can be drilled to form a hole for receiving an alignment finger of an inserter (discussed below). In one example, guide hole 148 and drill bit 138 can be sized to produce a 2.7 mm hole. Drill bit 138 can be advanced until the drill depth is achieved by a shoulder on drill bit 138 bottoming out on baseplate 142. In other embodiments, an etch can be provided on drill bet 138 to indicate the desired drill depth. Drilling of a 2.7 mm alignment hole can help facilitate orientation of augmented baseplate 52 during insertion. Drill guide 136 can then be removed from guide pin 102 and guide pin 102 can be removed from glenoid G.

Figure 8A:
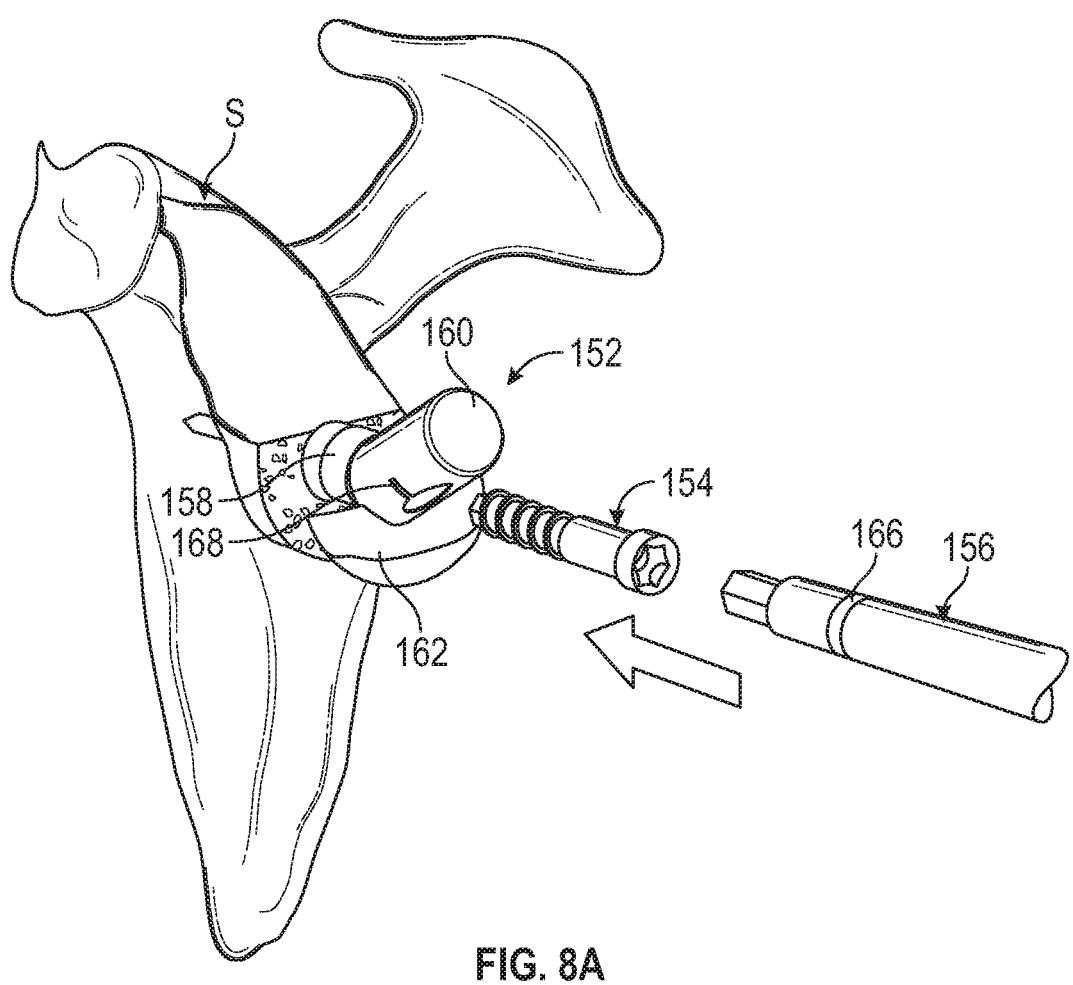
FIG. 8A is an exploded view of an augment ream guide, a fixation fastener and a driver instrument.
Figure 8B:
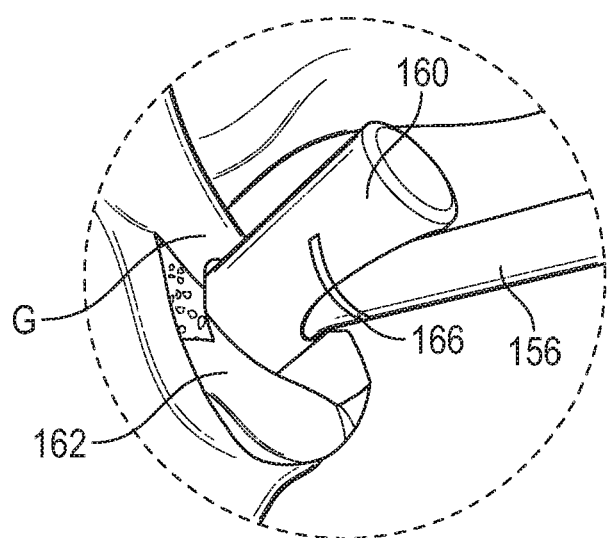
FIG. 8B is a perspective view of the augment ream guide seated on the partially reamed scapula with the driver instrument inserted into the augment ream guide.
Figure 8C:
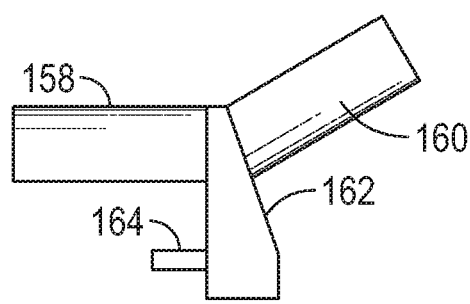
FIG. 8C is a side view of the augment ream guide of FIGS. 8A and 8B.

FIG. 8A is an exploded view of augment ream guide 152, fixation fastener 154 and driver instrument 156. FIG. 8B is a perspective view of augment ream guide 152 seated on partially reamed scapula S with driver instrument 156 inserted into augment ream guide 152. FIG. 8C is a side view of augment ream guide 152, which can include bone peg 158, guide peg 160, base 162 and alignment post 164. Glenoid G can include alignment hole 150 produced by drill bit 138 in the previous step.

Bone peg 158 can extend substantially perpendicularly from the bottom surface of base 162, while guide peg 160 can extend at an oblique angle to bone peg 160. Substantially perpendicular can include the central axis of bone peg 160 being disposed ninety degrees to the bottom surface of base 162, as well as the central axis being within five degrees of perpendicular. Substantial perpendicularity of bone peg 160 can facilitate easy insertion of augment ream guide 152 into central bore 124.

Guide pin 102 can be removed. The appropriately sized (10°, 20° or 30°) augment ream guide 152 can be placed on the prepared glenoid G taking care to align alignment hole 150 with alignment post 164 on ream guide 152. Next, bone peg 160 can be inserted into central bore 124 in glenoid G, and fixation fastener 154 can be inserted into guide peg 160 until it is fully seated within augment ream guide 152. Fixation fastener 154 can be inserted using a hex driver under hand power. Etch line 166 on drive instrument 156 can align with etch line 168 on ream guide 152 when completely seated. Fixation fastener 154 can be engineered with the same pitch as fixation fastener 60E (FIG. 3A) to help ensure every thread of fixation fastener 60E will engage undisturbed bone. Fixation fastener 154 can provide fixation of ream guide 152 during reaming for augmented baseplate 52.

Figure 9A:
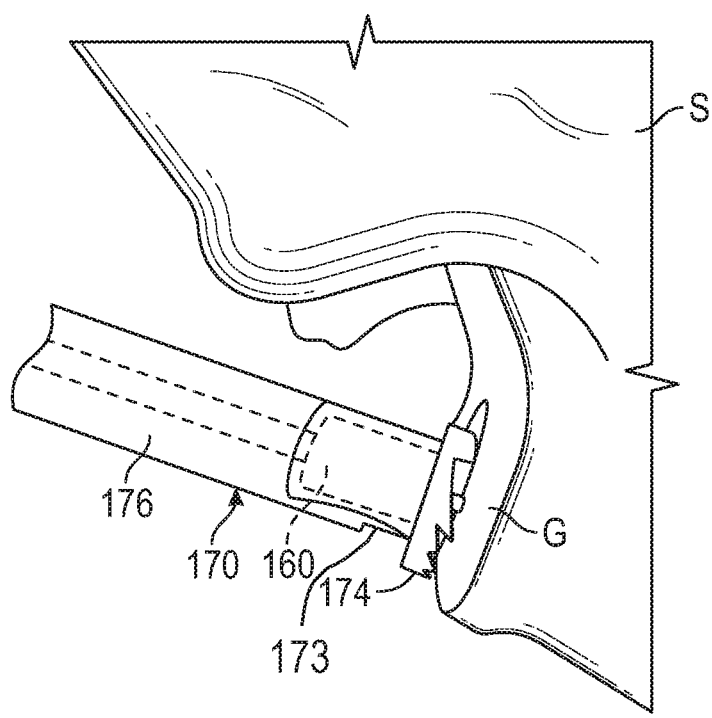
FIG. 9A is a perspective view of an augment reamer being advanced along the augment ream guide of FIGS. 8A-8C to further ream the partially reamed scapula.
Figure 9B:
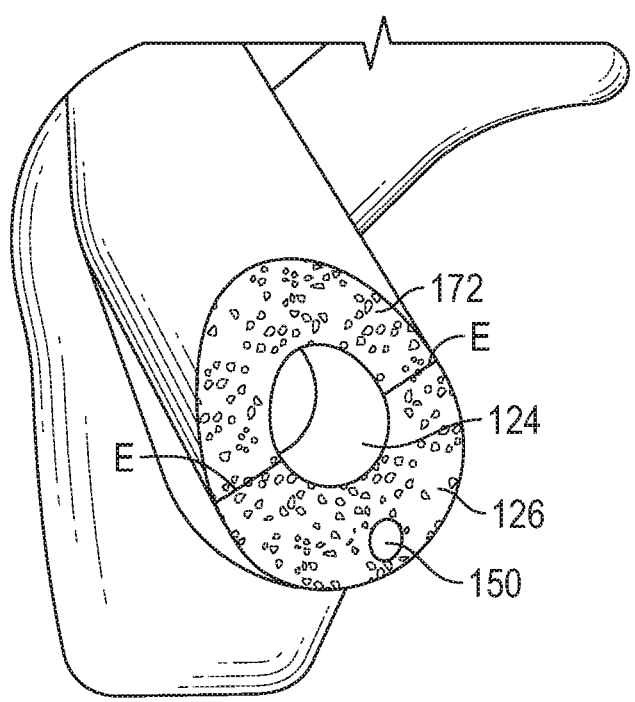
FIG. 9B is a close up view of the completely reamed scapula of FIG. 9A.

FIG. 9A is a perspective view of augment reamer 170 being advanced along augment ream guide 152 (shown in phantom) of FIGS. 8A-8C to further ream the partially reamed scapula S. FIG. 9B is a close up view of completely reamed scapula S of FIG. 9A including central bore 124, first reamed surface 126, alignment hole 150 and second reamed surface 172.

The appropriately sized (10°, 20° or 30°) augment reamer 170 can be placed over guide peg 160 of augment ream guide 152. Reamer 170 can include notch 173 that extends into shaft 176 head 174. In particular, a portion of the circumference of shaft 176 can be cut away at the end of shaft 176 that engages head 174, and head 174 can include a similarly located notch that extends into the circumference of head 174 at the same circumferential location as the cut away portion of shaft 176. The notch in head 174 can extend to the center of head 174 so that head 174 has a U shape. Configured as such, reamer 170 can be slipped over guide peg 160 without the axes of shaft 176 and guide peg 160 being coaxial. Thus, reamer 170 can be advanced normal to the face of glenoid G. Thus, reamer 170 can enter more directly into an incision in the patient and avoid surrounding tissues.

Reamer 170 can be fully captured on ream guide peg 160 before beginning to ream, such as by contacting reamer head 174 against glenoid G. Reamer shaft 176 can be rotated to remove bone. If necessary, glenoid osteophytes can be removed to allow proper seating of reamer 170. Reaming can continue to advance reamer head 174 until a shoulder within reamer shaft 176 bottoms out on ream guide peg 160 and the appropriate amount of bone has been prepared to accept the selected size of augmented baseplate 52. Ream guide 152 can be designed to allow minimal reaming of the bone necessary to seat augmented baseplate 52. Next, fixation fastener 154 (FIG. 8A) can be removed and augment ream guide 152 can also be removed. Glenoid G can subsequently can include second reamed surface 172 opposite first reamed surface 126. First and second reamed surfaces 126 and 172 can adjoin at edge E. Thus, in one example, glenoid G can now accept augmented baseplate 52. In particular, parallel surface 54A can abut first reamed surface 126 and oblique surface 54B can abut second reamed surface 172.

Figure 10A:
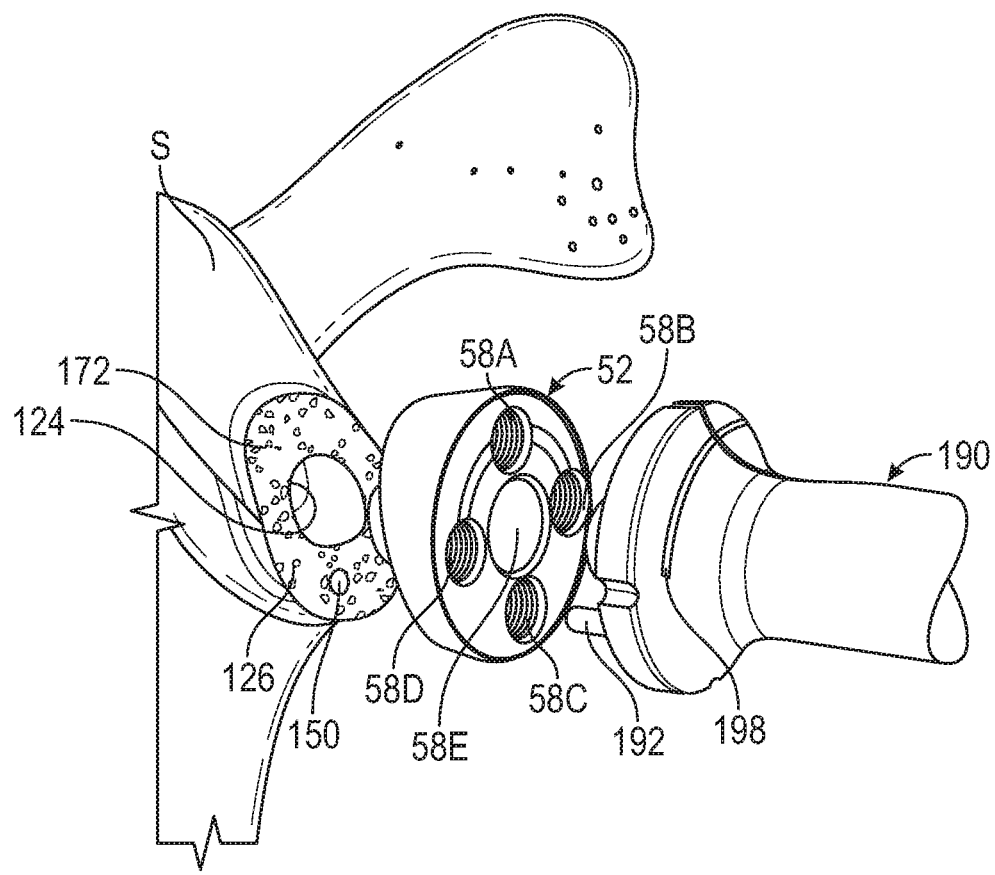
FIG. 10A is an exploded view of an alignment post of an augmented baseplate impactor being aligned with an augmented baseplate and the alignment hole of the scapula.
Figure 10B:
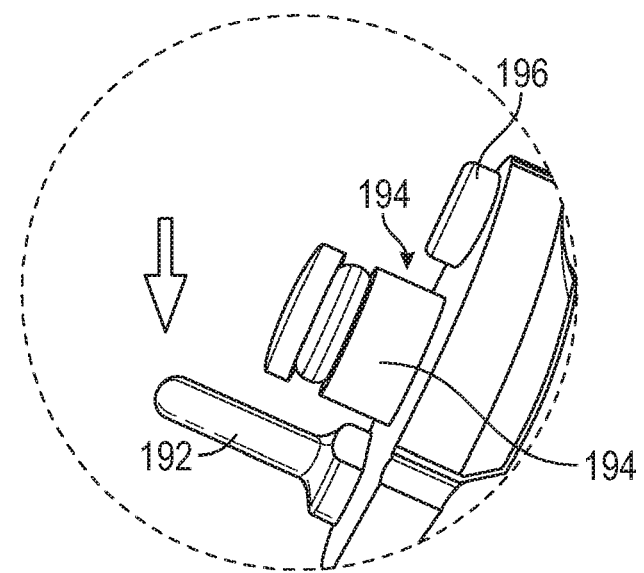
FIG. 10B is a perspective view of an impact face of the augmented baseplate impactor showing the alignment post, a center post and a peripheral post.

FIG. 10A is an exploded view of augmented baseplate impactor 190 and augmented baseplate 52. Augmented baseplate impactor 190 can include alignment post 192, which can be used to align augmented baseplate 52 with alignment hole 150. FIG. 10B is a perspective view of impact face 194 of augmented baseplate impactor 190 showing alignment post 192, center post 194 and peripheral post 196.

Augmented baseplate 52 can be placed onto impact face 194 of baseplate impactor 190. For example, central post 194 can be inserted into bore 58E in baseplate 52, while peripheral post 196 is inserted into bore 58A. Alignment post 192 can extend through bore 58C to be inserted into alignment hole 150. Additionally, proper orientation of impactor 190 can determined by aligning the augment of baseplate 52 (e.g. oblique surface 54B) with a corresponding "augment" label on inserter 190. When alignment post 192 is in the correct orientation, half-circle etch 198 on inserter 190 can align with second reamed surface 172.

Once aligned, augmented baseplate 52 can be impacted into glenoid G and remove augmented baseplate impactor 190. Parallel and oblique surfaces 54A, 54B of augmented baseplate 52 can or should be fully seated on first and second reamed surfaces 126, 172, respectively on the face of glenoid G. Fasteners 60A-60E can be used to secure baseplate 52 to scapula S, and glenosphere 62 can be attached to baseplate 52 via stem 64.

Visual confirmation can be attained by checking for gaps between the reamed surface of glenoid G and baseplate 52 at bores 58A-58D. A small nerve hook can be used to aid in confirming complete seating of baseplate 52. Due to the 10 degree inferior to superior orientation for the baseplate preparation, baseplate 52 may be partially or fully countersunk inferiorly. Guide pin 102 can be reinserted before impacting baseplate 52 if cannulated insertion is desired.

Figure 11:
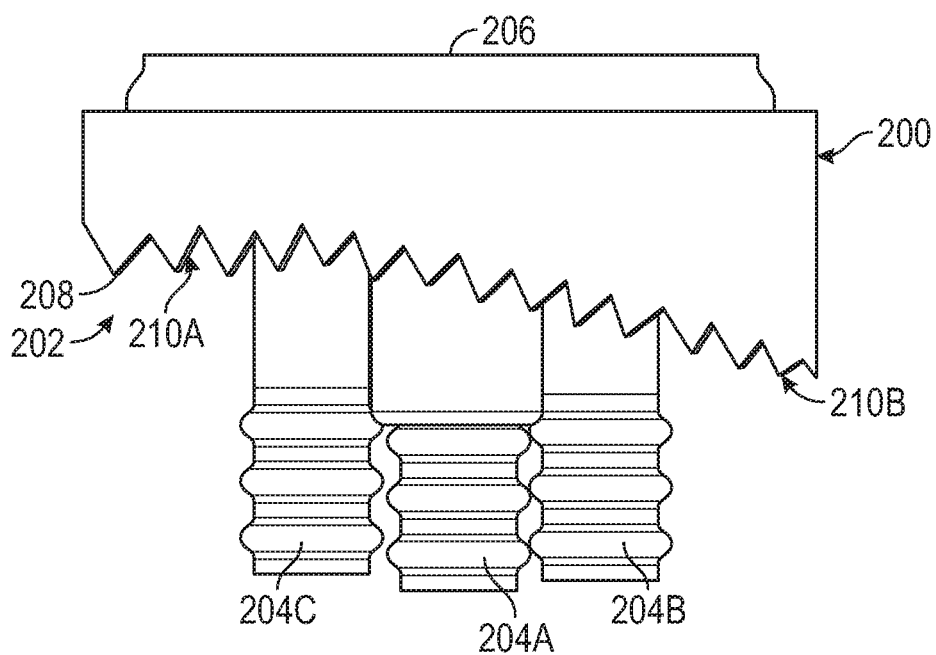
FIG. 11 is a perspective view of an augmented baseplate for an anatomic shoulder implant having an angled bone surface with fixation posts.

FIG. 11 is a perspective view of augmented baseplate 200 for an anatomic shoulder implant having angled bone surface 202 with fixation posts 204A-204C, Baseplate 200 can also include articular surface 206, which can be configured to directly engage a humeral head. Angled bone surface 202 can include crenellations or corrugations 208 that can be used to engage bone and promote bone growth. Angled bone surface 202 can include parallel surface 210A, which can be parallel to glenoid surface 206, and oblique surface 210B, which can be angled at an oblique angle relative to parallel surface 210A.

Glenoid G of scapula S can be prepared to mate with parallel surface 210A and oblique surface 211B, such as by reaming of glenoid G to form obliquely oriented planar bone surfaces. Oblique surface 210B can be located in different orientations on glenoid G, depending on the particular implant and particular patient. The methods, instruments and tools described herein, particularly with reference to FIGS. 12-18, facilitate implantation of augmented baseplate 200 onto scapula S in such a manner so as to minimize bone removal and subsequently align augmented baseplate so that surfaces 210A and 210B mate flush with prepared surfaces of glenoid G.

Figure 12:
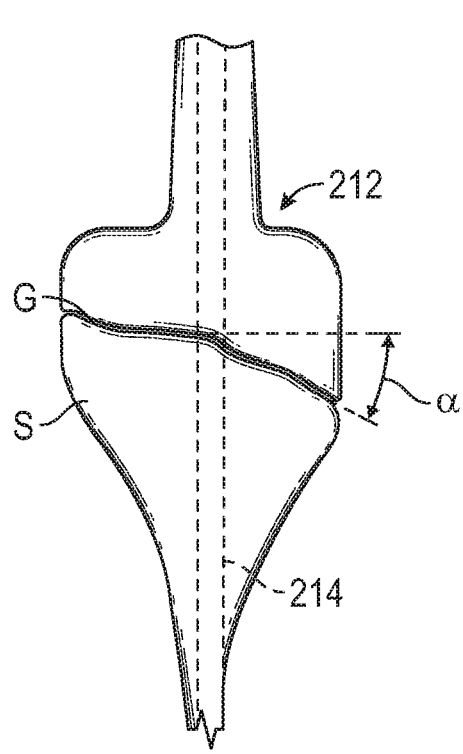
FIG. 12 is a schematic view of a patient-specific glenoid guide engaging a glenoid of a scapula to install a guide pin substantially parallel to an anatomic axis.

FIG. 12 is a schematic view of patient-specific glenoid guide 212 engaging glenoid G of a scapula to install guide pin 214 substantially parallel to the central axis of the vault of glenoid G. In the depicted example, glenoid G is classified as a Walch B2 glenoid, e.g., a retroverted glenoid with posterior rim erosion, or a bi-concave wear pattern with an alpha angle. Patient-specific glenoid guide 212 can be placed onto the face of glenoid G. Guide pin 214 can be inserted through glenoid guide 212 into the glenoid vault of glenoid G.

Figure 13:
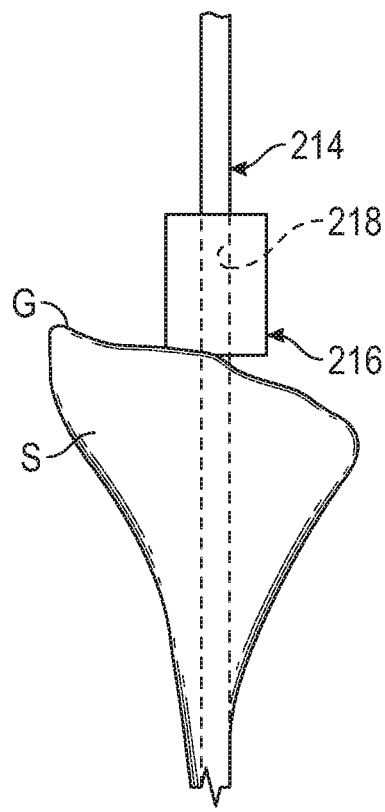
FIG. 13 is a schematic view of a depth stop being installed around the guide pin of FIG. 12.

FIG. 13 is a schematic view of depth stop 216 installed around guide pin 214 of FIG. 12. In one example, depth stop 216 can be patient-specific in that the length of depth stop 216 can be sized to allow a reamer to ream glenoid G to a depth based on a specific patient's bone defects, Depth stop 216 can include a central bore 218 to receive guide pin 214. The outer diameter of depth stop 216 can be sized to receive a socket of a corresponding reamer.

Figure 14:
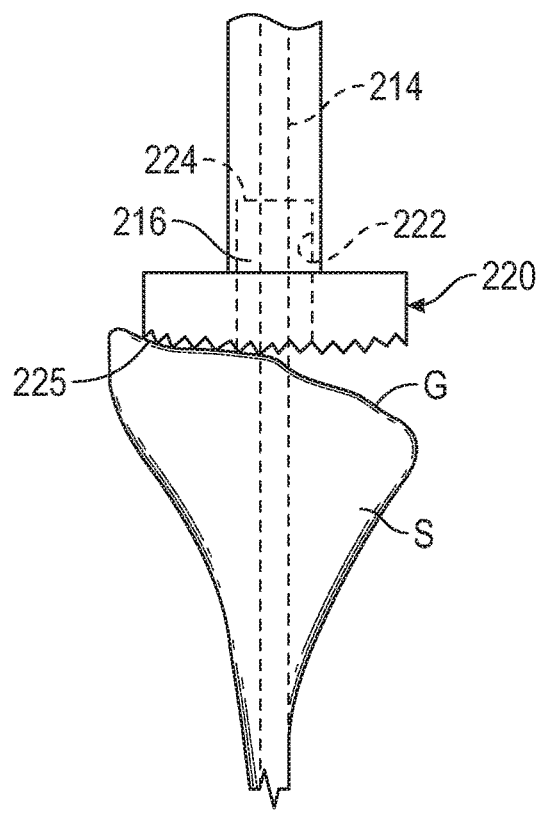
FIG. 14 is a schematic view of a reamer being installed around the guide pin and depth stop of FIG. 13.

FIG. 14 is a schematic view of reamer 220 installed around guide pin 214 and depth stop 216 of FIG. 13. Reamer 220 can be a standard face reamer that includes socket 222 for receiving depth stop 216. Reamer 220 can be advanced until end wall 224 of socket 222 engages the proximal surface of depth stop 216. Reamer 220 can form first prepared surface 225 on glenoid G.

Figure 15:
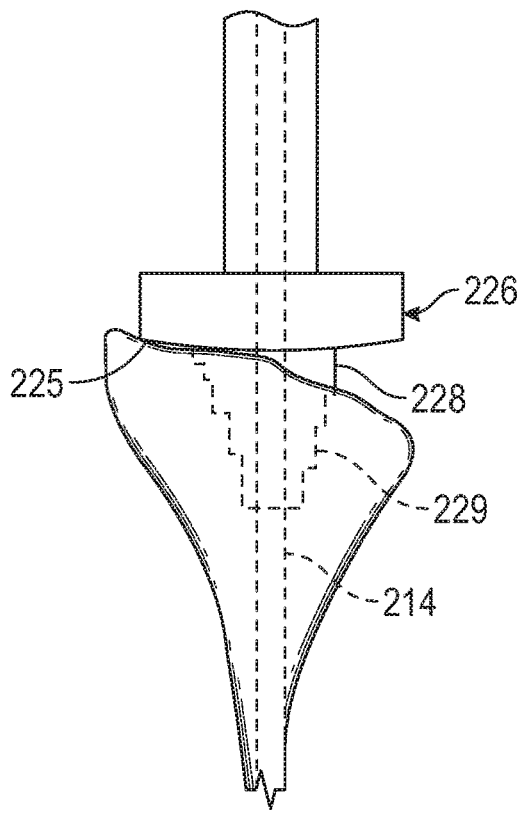
FIG. 15 is a schematic view of a boss and post reamer being installed around the guide pin of FIG. 13.

FIG. 15 is a schematic view of boss and post reamer 226 installed around guide pin 214 of FIG. 13. Post reamer 226 can include central portion 228, which can be configured as a reamer, drill or a rasp to remove bone from glenoid G. In particular, central portion 228 can be stepped to provide bore 229 having various diameters within scapula S. In particular, central portion 228 can be stepped to provide progressively smaller diameter bore segments within scapula S the deeper bore 229 goes into the bone. Central portion 228 can be shaped to mate with the shape of fixation post 204A of augmented baseplate 200.

Figure 16:
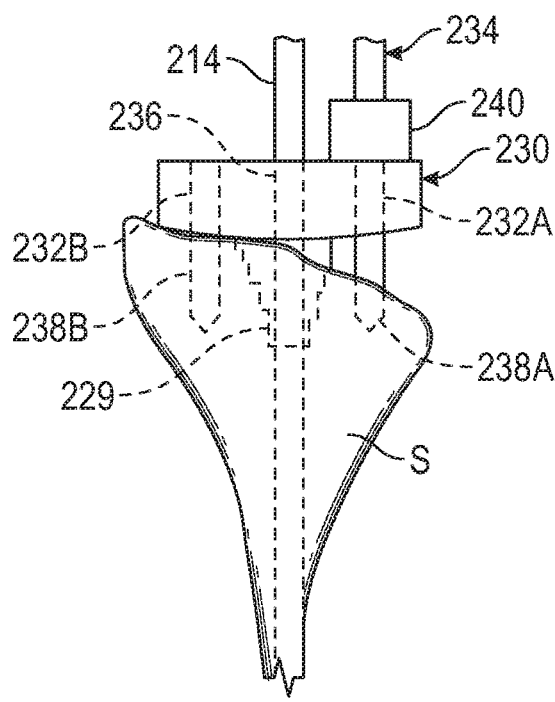
FIG. 16 is a schematic view of a peripheral post reamer guide being installed around the guide pin of FIG. 13.

FIG. 16 is a schematic view of peripheral post guide 230 installed around guide pin 214 of FIG. 13. Post guide 230 includes sockets 232A and 232B for receiving drill or reamer 234, as well as socket 236 for receiving guide pin 214. Sockets 232A and 232B are positioned relative to guide pin 214 in order to place bores 238A and 238B relative to bore 229 in locations to correspond to posts 204A 204C on baseplate 200. Thus, after post reamer 226 is removed from guide pin 214, socket 236 of peripheral post guide 230 can be slipped around guide pin 214 and reamer 234 can be used to make bores 238A and 238B using sockets 232A and 232B, respectively. Drill 234 can include stop 240 to ensure that bores 238A and 238B are reamed to the depth of posts 204B and 204C. Bores 238A and 238B can be shaped to mate with the shape of fixation posts 204B and 204C, respectively.

Figure 17:
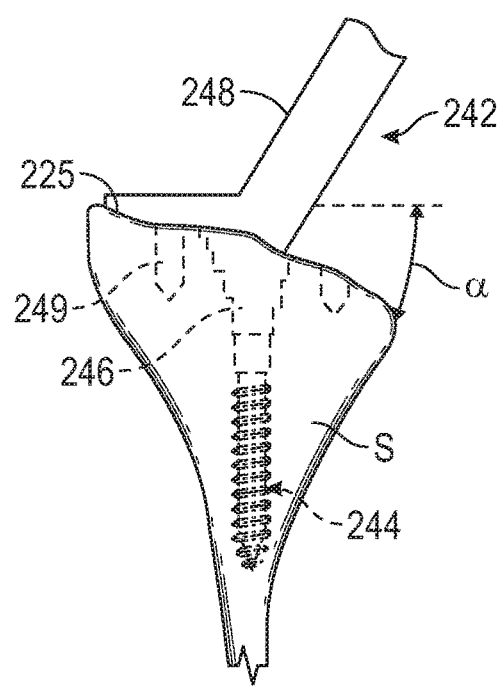
FIG. 17 is a schematic view of a patient-specific angled ream guide being installed with a compression screw that follows the path of the guide pin of FIG. 13.

FIG. 17 is a schematic view of patient-specific angled ream guide 242 installed with compression screw 244 that follows the path of the guide pin of FIG. 13. Guide pin 214 can be removed and angled ream guide 242 can be inserted into bore 229. Compression screw 244 can be inserted into ream guide 242 and threaded into scapula S along the path of guide pin 214 to stabilize ream guide 242 for reaming. Angled ream guide 242 can be configured similarly to ream guide 152 of FIGS. 8A 8C. Ream guide 242 can include bone post 246 that is shaped to at least partially fill bore 229 and that includes a central bore for receiving compression screw 244. Guide post 248 can extend from bone post 246 at angle α, which can correspond to the angle between surfaces 210A and 210B of augmented baseplate 200. Alignment post 249 can be connected to ream guide 242 to orient guide post 248 in the correct direction. Alignment post 249 can have the shape of 204C and bone post 246 can have the shape of post 204A.

Figure 18:
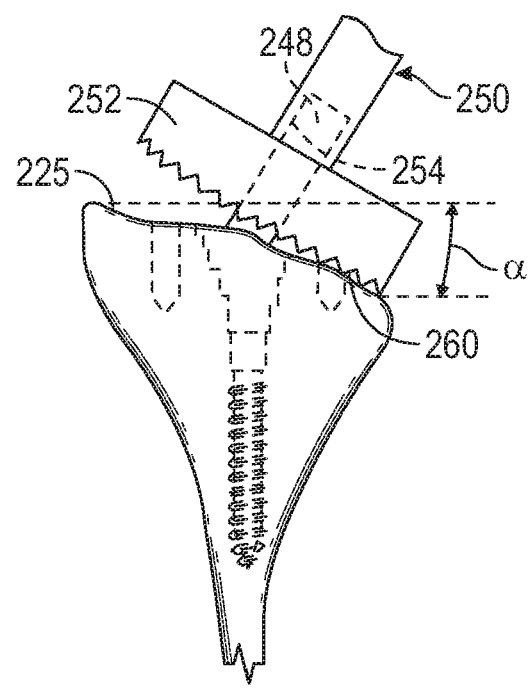
FIG. 18 is a schematic view of a reamer being installed around the angled ream guide of FIG. 17.

FIG. 18 is a schematic view of reamer 250 installed around guide post 248 of angled ream guide 242 of FIG. 17. Reamer head 252 includes socket 254 to receive guidepost 248. Using shaft 256, reamer head 252 can be rotated to form second prepared surface 260 on glenoid G. Guide post 248 can act as a depth stop to limit advancement or reamer 250. Reamer 250 thereby produces second prepared surface 260 at angle α relative to first prepared surface 225 so that prepared surfaces 225 and 260 mate with surfaces 210A and 210B, respectively of baseplate 200.

Figure 19:
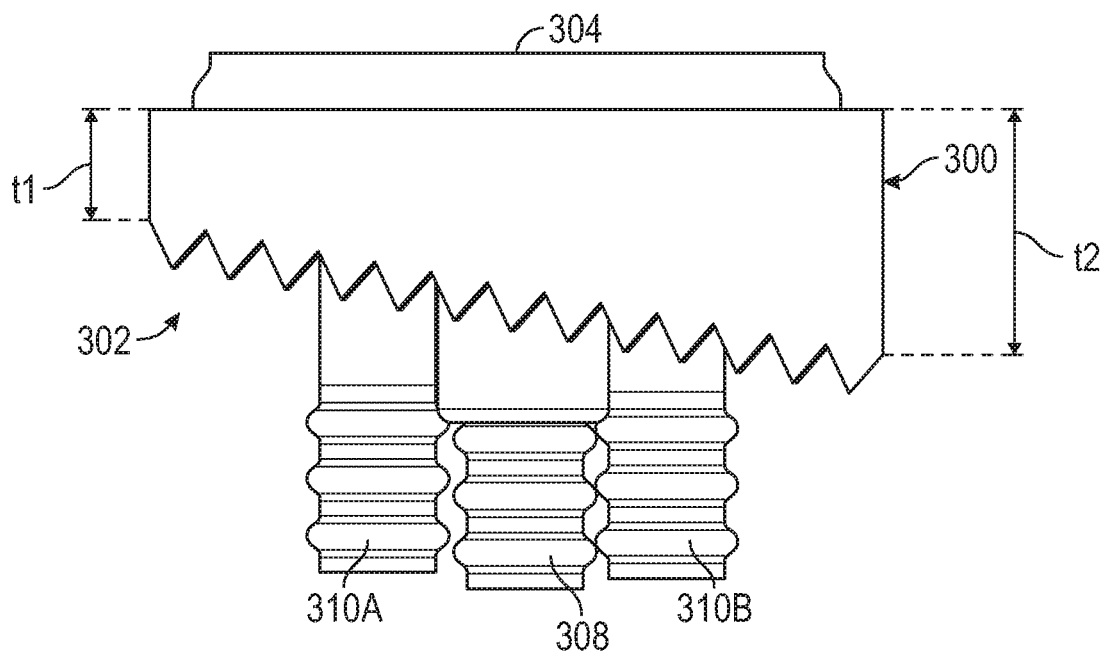
FIG. 19 is a perspective view of an augmented baseplate for a reverse shoulder implant having a slanted or sloped bone surface with fixation posts.

FIG. 19 is a perspective view of augmented glenoid implant 300 having slanted bone surface 302. Glenoid implant 300 can also include surface 304, center post 308, and peripheral posts 310A and 310B. Slanted bone surface 302 can form first thickness t1 with surface 304 at a first end and second thickness t2 with surface 304 at a second end.

Glenoid G of scapula S can be prepared to mate with slanted bone surface 302, such as by partially reaming of glenoid G at an angle to remove damaged bone. Slanted bone surface 302 of augmented baseplate 300 can then partially mate flush with the surface of glenoid G reamed at an angle and partially mate flush with a naturally angled, undreamed surface of glenoid G. Alternatively, substantially all of glenoid G can be reamed at the desired angle to mate with slanted bone surface 302. The methods, instruments and tools described herein, particularly with reference to FIGS. 20-25, facilitate implantation of augmented baseplate 300 onto scapula S in such a manner so as to minimize bone removal and subsequently align augmented baseplate 300 so that slanted bone surface 302 mates flush with the prepared surface of glenoid G.

Figure 20:
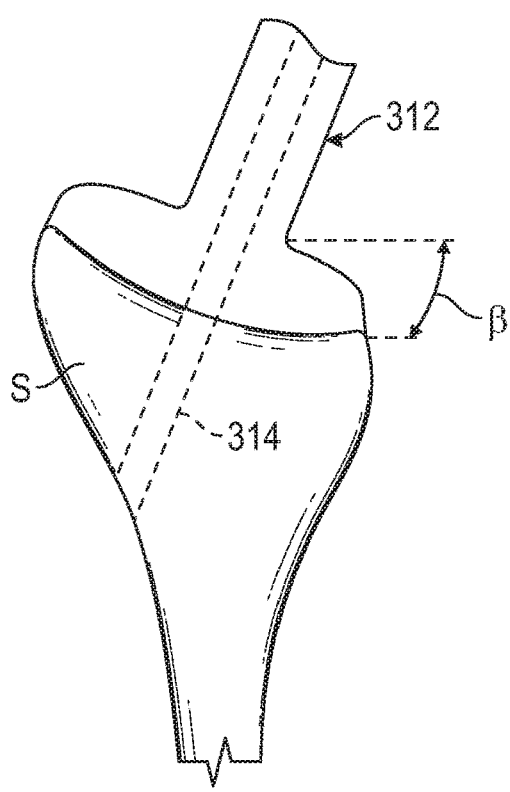
FIG. 20 is a schematic view of a patient-specific glenoid guide engaging a glenoid of a scapula to install a guide pin at an angle.

FIG. 20 is a schematic view of a patient-specific glenoid guide 312 engaging glenoid G of scapula S to install guide pin 314 at angle β. In the depicted example, glenoid G is classified as a Walch B1 glenoid, e.g., a glenoid having a narrow posterior joint space, subchondral sclerosis and osteophytes or a sloped wear pattern with a beta angle. Patient-specific glenoid guide 312 is placed onto the face of glenoid G. Guide pin 314 is inserted through glenoid guide 312 into the glenoid vault of glenoid G. Glenoid guide 312 mates with glenoid G to align guide pin 314 at angle β, which can be the pathologic angle of glenoid G. Angle β can be predetermined from a surgical plan to allow a reamer to engage a high side of glenoid G having bone damage.

Figure 21:
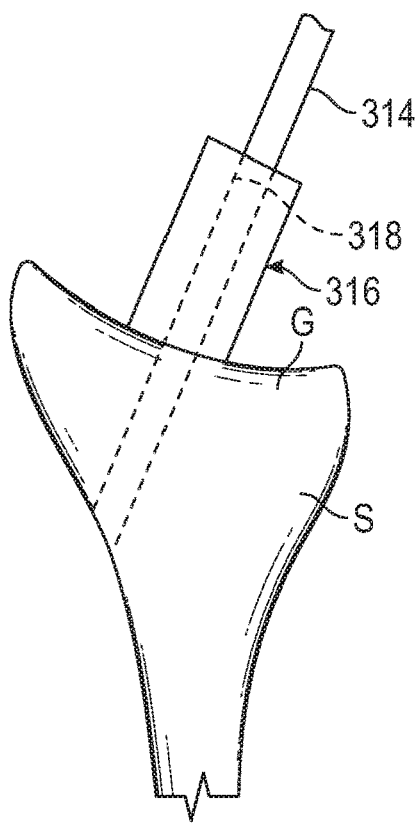
FIG. 21 is a schematic view of a depth stop surrounding the guide pin of FIG. 20.

FIG. 21 is a schematic view of depth stop 316 surrounding guide pin 314 of FIG. 20. In one example, depth stop 316 can be patient-specific in that the length of depth stop 316 can be sized to allow a reamer to ream glenoid G to a depth based on a specific patient's bone defects. Depth stop 316 can include central bore 318 to receive guide pin 314. The outer diameter of depth stop 316 can be sized to receive a socket of a corresponding reamer.

Figure 22:
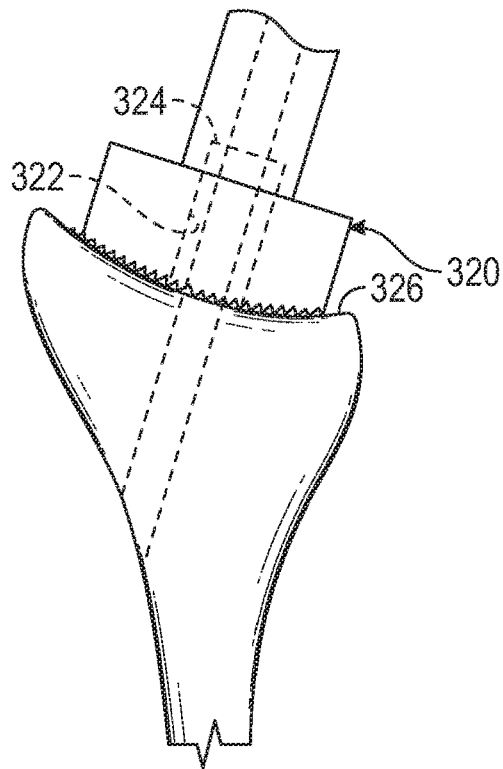
FIG. 22 is a schematic view of a reamer being advanced onto the guide pin of FIG. 20 to surround the depth stop and at least partially ream the glenoid.

FIG. 22 is a schematic view of reamer 320 being advanced onto guide pin 314 of FIG. 20 to surround depth stop 316 and at least partially ream glenoid G. Reamer 320 can be a standard face reamer that includes socket 322 for receiving depth stop 316. Reamer 320 can be advanced until end wall 324 of socket 322 engages the proximal surface of depth stop 316. Reamer 320 can form prepared surface 326 on glenoid G. The high side of the glenoid G can be reamed to remove damaged bone in glenoid G.

Figure 23:
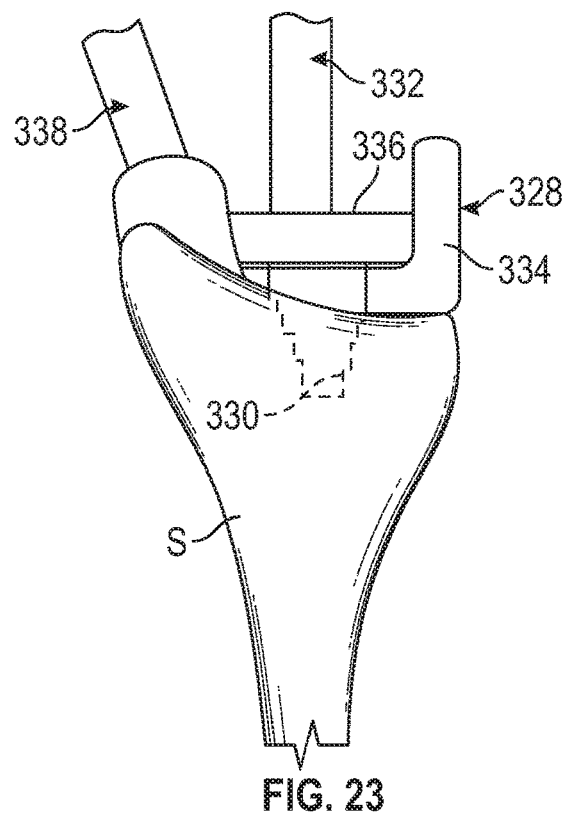
FIG. 23 is a schematic view of a patient-specific drill guide mated to the partially reamed glenoid of FIG. 22 to form a central post bore in conjunction with a reamer.

FIG. 23 is a schematic view of a patient-specific drill guide 328 mated to partially reamed glenoid G of FIG. 22 to form central post bore 330 in conjunction with drill or reamer 332. Drill guide 328 can include base 334, which can be patient-specific to mate with partially reamed glenoid G, and cup 336, which can be shaped to receive reamer 332 and positioned to align central post bore 330 in scapula S. Base 334 is shaped to align central post bore 330 along the anatomic axis of scapula S while accounting for the fact that base 334 can be slanted and non-perpendicular to the anatomic axis. Base 334 can register on a periphery of glenoid G and a portion of the reamed face of glenoid G. Drill guide 328 can also include handle shaft 338 that can allow a surgeon to position and steady base 334 for performing reaming. Reamer 332 can be a standard boss reamer.

Figure 24:
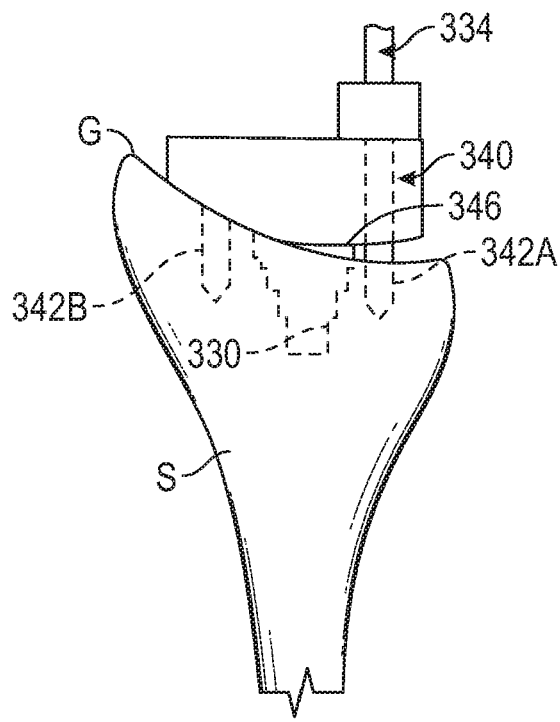
FIG. 24 is a schematic view of a patient-specific peripheral post reamer guide being advanced into the reamed central post bore of FIG. 23 to form peripheral bores in conjunction with a reamer.

FIG. 24 is a schematic view of a patient-specific peripheral post reamer guide 340 being advanced into reamed central post bore 330 of FIG. 23 to form peripheral bores 342A and 342B in conjunction with drill or reamer 344. Reamer guide 340 can include center peg 346 that can be shaped to mate with central post bore 330 to align peripheral bores 348A and 348B with respect to glenoid G. Reamer 344 can be a standard reamer. Alternatively, a drill may be used. Patient-specific peripheral post reamer guide 340 can allow for reaming of peripheral bores 342A and 342B without the need for inserting additional guide pins into glenoid G.

Figure 25:
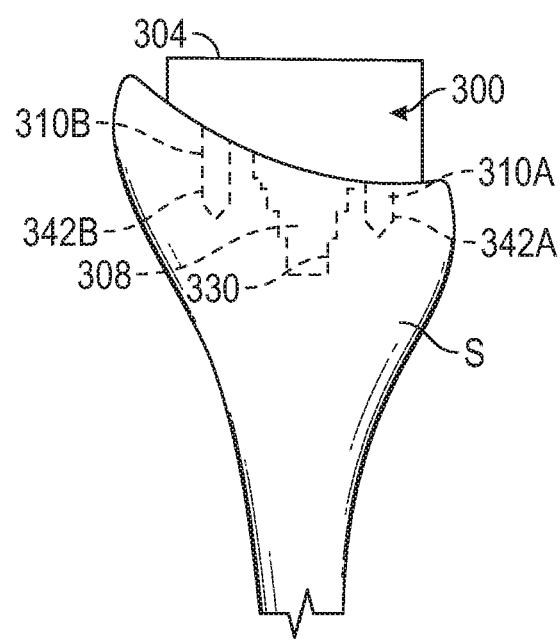
FIG. 25 is a schematic view of the augmented baseplate of FIG. 19 mounted onto the partially reamed glenoid so that slanted bone face and fixation posts mate with the prepared glenoid.

FIG. 25 is a schematic view of the augmented baseplate 300 of FIG. 19A mounted onto partially reamed glenoid G so that slanted bone face 302 and fixation posts 308, 310A and 310B mate with prepared glenoid G. Before augmented baseplate 300 is implanted, preparation of glenoid G can be performed with a patient-specific glenoid trial having a full augment (not shown). After confirmation of the reaming of glenoid G, posts 308, 310A and 310B of augmented baseplate 300 can be inserted into bores 330, 342A and 342B, respectively, of scapula S. A standard impactor can be used to insert augmented baseplate 300 and bone cement can also be used in bores 330, 342A and 342B. In one example, augmented baseplate 300 will start at an anterior side of glenoid G and angle or slope to the posterior side, as opposed to the procedure described with reference to FIGS. 11-18 where the angle or slope starts at the midline of glenoid G.

The methods, implants and tools described herein are advantageous over previous systems. For example, the patient-specific augment reamer guides can allow for precise reaming of a glenoid with minimal bone removal, and can allow for accurate fitting with patient-specific implants. The patient-specific guides can allow for placement of guide pins, such as Steinmann Pins, at the angle of pathologic glenoid for face reaming, or to place guide pins along the main axis of the glenoid vault. The patient-specific guides can allow for reaming of glenoid bosses (e.g., with standard reamers) and can be made so as to not require placement of a second pin in the glenoid. The patient-specific augmented implants can be made for various types of glenoid deficiencies, such as B1, B2 or other glenoid classification (anatomic or reverse).

Various Notes & Examples

Example 1 can include or use subject matter such as a glenoid implant, comprising: a body comprising: an articular surface configured to mate with or receive another component configured to mate with a complimentary component; and a scapula-engaging surface opposite the articular surface, the scapula engaging surface including first and second portions angled relative to each other; and a fixation feature extending from the scapula-engaging surface.

Example 2 can include, or can optionally be combined with the subject matter of Example 1, to optionally include a body and fixation feature that are made from porous metal material.

Example 3 can include, or can optionally be combined with the subject matter of one or any combination of Examples 1 or 2 to optionally include a body including a sidewall having a first thickness at the first portion of the scapula-engaging surface and a second thickness at the second portion of the scapula-engaging surface, the second thickness being greater than the first thickness.

Example 4 can include, or can optionally be combined with the subject matter of one or any combination of Examples 1 through 3 to optionally include an edge between the first and second portions extends across a midline of the scapula-engaging surface between the first and second portions.

Example 5 can include, or can optionally be combined with the subject matter of one or any combination of Examples 1 through 4 to optionally include first and second portions that are each planar.

Example 6 can include, or can optionally be combined with the subject matter of one or any combination of Examples 1 through 5 to optionally include first and second portions that are angled relative to each other at an angle in the range of approximately ten degrees to approximately thirty degrees.

Example 7 can include, or can optionally be combined with the subject matter of one or any combination of Examples 1 through 6 to optionally include a fixation feature that comprises a center boss for receiving a fixation fastener.

Example 8 can include, or can optionally be combined with the subject matter of one or any combination of Examples 1 through 7 to optionally include a fixation feature comprising a plurality of posts.

Example 9 can include, or can optionally be combined with the subject matter of one or any combination of Examples 1 through 8 to optionally include a scapula-engaging surface that includes corrugations.

Example 10 can include or use subject matter such as a method for implanting a scapular baseplate in a shoulder arthroplasty, the method comprising: inserting a guide pin into a glenoid of the scapula using a guide instrument; preparing a first portion of the glenoid to form a planar bone surface using the guide pin; forming a first bore into the glenoid located approximately at the guide pin; forming a second bore into the glenoid offset from the first bore; inserting an augment ream guide into the first bore and the second bore; and preparing a second portion of the glenoid to form an angled bone surface relative to the planar bone surface using the augment ream guide.

Example 11 can include, or can optionally be combined with the subject matter of Example 10, to optionally include forming the first bore into the glenoid comprises positioning a reamer over the guide pin to ream the first bore while preparing the first portion of the glenoid; and forming the second bore into the glenoid comprises positioning a drill guide over the guide pin after removing the reamer and drilling the second bore.

Example 12 can include, or can optionally be combined with the subject matter of one or any combination of Examples 10 or 11 to optionally include forming the first bore into the glenoid by positioning a boss and post reamer over the guide pin to ream the first bore after preparing the first portion of the glenoid; and forming the second bore into the glenoid by positioning a drill guide over the guide pin after removing the reamer and drilling the second bore.

Example 13 can include, or can optionally be combined with the subject matter of one or any combination of Examples 10 through 12 to optionally include a guide instrument that is patient-specific to mate with the glenoid.

Example 14 can include, or can optionally be combined with the subject matter of one or any combination of Examples 10 through 13 to optionally include a guide instrument that positions the guide pin approximately parallel to a main axis of a vault of the glenoid, the planar bone surface is approximately perpendicular to the main axis, and the angled bone surface is angled relative to the planar bone surface at an angle in the range of approximately ten degrees to approximately degrees.

Example 15 can include, or can optionally be combined with the subject matter of one or any combination of Examples 10 through 14 to optionally include preparing a first portion of the glenoid to form a planar bone surface by at least partially reaming the glenoid to approximately fifty percent of a surface area of the glenoid.

Example 16 can include, or can optionally be combined with the subject matter of one or any combination of Examples 10 through 15 to optionally include preparing a first portion of the glenoid to form a planar bone surface by inserting a post of the augment ream guide into a notch in a reamer head and shaft of a reamer.

Example 17 can include, or can optionally be combined with the subject matter of one or any combination of Examples 10 through 16 to optionally include positioning a depth stop over the wide pin to limit a depth to which the glenoid can be reamed.

Example 18 can include or use subject matter such as a ream guide for a shoulder arthroplasty procedure, the ream guide comprising: a base having a first surface and a second surface; a bone peg extending substantially perpendicularly from the first surface; an alignment peg extending from the first surface spaced from the bone peg; and a guide peg extending from the second surface opposite the bone peg at an oblique angle to the bone peg.

Example 19 can include, or can optionally be combined with the subject matter of Example 18, to optionally include a guide peg that includes an aperture extending into the bone peg.

Example 20 can include, or can optionally be combined with the subject matter of one or any combination of Examples 18 or 19 to optionally include a second surface that is angled relative to the first surface.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A ream guide for a shoulder arthroplasty procedure, the ream guide comprising:
a base having a first surface and a second surface;
a bone peg extending substantially perpendicularly from the first surface;
an alignment peg extending from the first surface spaced from the bone peg; and a guide peg comprising a sidewall extending from the second surface opposite the bone peg at an oblique angle to the bone peg;
wherein the guide peg includes an aperture extending into the sidewall of the guide peg, through the base and into and out of the bone peg.

2. The ream guide of claim 1, wherein the second surface is angled relative to the first surface.

3. The ream guide of claim 2, wherein the second surface is angled relative to the first surface to define the oblique angle.

4. The ream guide of claim 1, wherein the oblique angle comprises ten degrees, twenty degrees or thirty degrees.

5. The ream guide of claim 1, wherein the guide peg includes a first indicator line adjacent the aperture.

6. The ream guide of claim 1, wherein the aperture includes an opening in the guide peg such that the aperture extends through the bone peg.

7. The ream guide of claim 1, wherein the bone peg extends within five degrees of perpendicular from the first surface.

8. A system for performing a shoulder arthroplasty procedure, the system comprising:
a ream guide comprising:
a base extending along a first axis, the base comprising:
first surface disposed perpendicular to the first axis; and
a second surface opposite the first surface and disposed at an oblique angle to the first axis;
a bone peg extending substantially perpendicularly from the first surface;
a guide peg extending substantially perpendicularly from the second surface; and
a fastener bore extending into the bone peg; and
a reamer comprising:
a cannulated shaft extending along a second axis;
a reamer head disposed at an end of the cannulated shaft, the reamer head configured to cut bone substantially perpendicular to the second axis; and
a notch extending into the cannulated shaft proximate the reamer head to allow the guide peg to be received into the cannulated shaft.

9. The system of claim 8, wherein the fastener bore includes an opening such that the fastener bore extends through the bone peg.

10. The system of claim 8, wherein the ream guide further comprises an alignment peg extending from the second surface opposite the bone peg at an oblique angle to the bone peg.

11. The system of claim 8, further comprising a glenoid implant comprising a scapula-engaging surface having first and second portions that are angled relative to each other at an angle equal to the oblique angle.

12. The system of claim 8, further comprising a fastener driver instrument configured to guide a fastener into the fastener bore.

13. The system of claim 12, wherein the ream guide comprises a first indicator mark intersecting the fastener bore.

14. The system of claim 13, wherein the fastener driver instrument includes a second indicator mark configured to align with the first indicator mark when the fastener is properly seated in the fastener bore of the ream guide.

15. A ream guide system for a shoulder arthroplasty procedure, the ream guide system comprising:
a ream guide comprising:
a base having a first surface and a second surface;
a bone peg extending substantially perpendicularly from the first surface;
an alignment peg extending from the first surface spaced from the bone peg; and
a guide peg extending from the second surface opposite the bone peg at an oblique angle to the bone peg, wherein the guide peg comprises:
an aperture extending into the bone peg; and
a first indicator line adjacent the aperture;
a reamer configured to receive the guide peg and ream flush with the second surface; and
a fastener driver instrument configured to guide a fastener into the aperture, the fastener driver instrument including a second indicator line configured to align with the first indicator line when the fastener is properly seated in the ream guide.

16. The ream guide system of claim 15, further comprising:
the fastener for insertion into the aperture.

17. The ream guide system of claim 15, further comprising a glenoid implant having a scapula-engaging surface having first and second portions that are angled relative to each other at an angle equal to the oblique angle.

* * * * *